(12) United States Patent
Godrich et al.

(10) Patent No.: US 11,456,077 B2
(45) Date of Patent: *Sep. 27, 2022

(54) SYSTEMS AND METHODS FOR PROCESSING ELECTRONIC IMAGES

(71) Applicant: PAIGE.AI, Inc., New York, NY (US)

(72) Inventors: Ran Godrich, New York, NY (US); Jillian Sue, New York, NY (US); Leo Grady, Darien, CT (US); Thomas Fuchs, New York, NY (US)

(73) Assignee: Paige.AI, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/530,028

(22) Filed: Nov. 18, 2021

(65) Prior Publication Data

US 2022/0076416 A1 Mar. 10, 2022

Related U.S. Application Data

(63) Continuation of application No. 17/377,260, filed on Jul. 15, 2021, now Pat. No. 11,210,787, which is a (Continued)

(51) Int. Cl.
*G06T 7/00* (2017.01)
*G06N 20/00* (2019.01)
(Continued)

(52) U.S. Cl.
CPC ........... *G16H 50/20* (2018.01); *G06K 9/6256* (2013.01); *G06N 20/00* (2019.01); *G06T 7/0012* (2013.01);
(Continued)

(58) Field of Classification Search
None
See application file for complete search history.

(56) References Cited

U.S. PATENT DOCUMENTS

2016/0364526 A1* 12/2016 Reicher ............... G06K 9/6227
2017/0262633 A1    9/2017 Miserendino et al.
(Continued)

FOREIGN PATENT DOCUMENTS

JP    2016126491     7/2016
WO    2019084697 A1  5/2019

OTHER PUBLICATIONS

International Search Report and Written Opinion issued in International Application PCT/US2020/035295, dated Aug. 17, 2020.

*Primary Examiner* — Santiago Garcia
(74) *Attorney, Agent, or Firm* — Bookoff McAndrews, PLLC

(57) ABSTRACT

An image processing method including identifying, using a machine learning system, an area of interest of a target image by analyzing microscopic features extracted from multiple image regions in the target image, the machine learning system being generated by processing a plurality of training images each comprising an image of human tissue and a diagnostic label characterizing at least one of a slide morphology, a diagnostic value, a pathologist review outcome, and an analytic difficulty; determining, using the machine learning system, a probability of a target feature being present in the area of interest of the target image based on an average probability; and determining, using the machine learning system, a prioritization value, of a plurality of prioritization values, of the target image based on the probability of the target feature being present in the target image.

16 Claims, 14 Drawing Sheets

Related U.S. Application Data continuation of application No. 16/887,855, filed on May 29, 2020.

(60) Provisional application No. 62/855,199, filed on May 31, 2019.

(51) Int. Cl.
| | |
|---|---|
| *G16H 50/20* | (2018.01) |
| *G16H 70/60* | (2018.01) |
| *G16H 40/20* | (2018.01) |
| *G16H 10/40* | (2018.01) |
| *G16H 30/40* | (2018.01) |
| *G16H 70/20* | (2018.01) |
| *G16B 40/20* | (2019.01) |
| *G06K 9/62* | (2022.01) |

(52) U.S. Cl.
CPC ............ *G16B 40/20* (2019.02); *G16H 10/40* (2018.01); *G16H 30/40* (2018.01); *G16H 40/20* (2018.01); *G16H 70/20* (2018.01); *G16H 70/60* (2018.01); *G06T 2207/10056* (2013.01); *G06T 2207/20081* (2013.01); *G06T 2207/30024* (2013.01); *G06T 2207/30096* (2013.01); *G06T 2207/30204* (2013.01); *G06V 2201/03* (2022.01); *G06V 2201/04* (2022.01)

(56) References Cited

U.S. PATENT DOCUMENTS

| | | | |
|---|---|---|---|
| 2017/0270666 A1* | 9/2017 | Barnes | G16H 50/30 |
| 2018/0210874 A1 | 7/2018 | Fuxman et al. | |
| 2019/0164287 A1* | 5/2019 | Gregson | G06T 7/0014 |
| 2019/0228524 A1 | 7/2019 | Chen et al. | |
| 2019/0340752 A1 | 11/2019 | Brestel et al. | |
| 2020/0185084 A1 | 6/2020 | Syeda-Mahmood et al. | |
| 2020/0381122 A1* | 12/2020 | Godrich | G06T 7/0012 |
| 2020/0388033 A1* | 12/2020 | Matlock | G06V 10/82 |
| 2020/0394825 A1* | 12/2020 | Stumpe | G06V 10/82 |
| 2020/0410683 A1* | 12/2020 | Hu | A61B 5/055 |
| 2021/0005308 A1* | 1/2021 | Klaiman | G06T 7/0012 |
| 2021/0117729 A1* | 4/2021 | Bharti | G06T 7/0012 |
| 2021/0118136 A1* | 4/2021 | Hassan-Shafique | G16B 40/00 |
| 2021/0193323 A1* | 6/2021 | Jain | G16H 50/70 |
| 2021/0249118 A1* | 8/2021 | Papagiannakis | G16H 30/40 |
| 2021/0259660 A1* | 8/2021 | Bharat | A61B 8/085 |
| 2021/0272694 A1* | 9/2021 | Madabhushi | G16H 50/20 |
| 2021/0343004 A1* | 11/2021 | Luengo Hendriks | G06T 7/0012 |
| 2021/0391078 A1* | 12/2021 | Kim | G16H 30/40 |

* cited by examiner

SYSTEMS AND METHODS FOR PROCESSING ELECTRONIC IMAGES

RELATED APPLICATION

This application is a continuation of and claims the benefit of priority to nonprovisional U.S. patent application Ser. No. 17/377,260, filed Jul. 15, 2021, which is a continuation of U.S. application Ser. No. 16/887,855, filed May 29, 2020, which claims the benefit of priority from U.S. Provisional Application No. 62/855,199, filed May 31, 2019, all of which are herein incorporated by reference in their entirety.

FIELD OF THE DISCLOSURE

Various embodiments of the present disclosure pertain generally to image-based slide prioritization, streamlining a digital pathology workflow, and related image processing methods. More specifically, particular embodiments of the present disclosure relate to systems and methods for providing an automatic prioritization process for preparing, processing, and reviewing images of slides of tissue specimens.

BACKGROUND

There is no standardized or efficient way to prioritize the review of images of tissue specimens for pathology patient cases. By extension, there is no standardized process for reviewing pathology slides. In some academic institutions, pathology trainees may perform a preliminary review of patient cases, triaging and prioritizing cases with significant findings and/or which require additional diagnostic workup (e.g., immunohistochemical stains, recuts, molecular studies, special stains, intradepartmental consultation). Meanwhile, patient diagnosis may involve using digitized pathology slides for a primary diagnosis. A desire exists for a way to expedite or streamline the slide preparation process. A desire further exists for a way to ensure that pathology slides have sufficient information to render a diagnosis, by the time the slides are reviewed by a pathologist.

SUMMARY

According to certain aspects of the present disclosure, systems and methods are disclosed for processing an image corresponding to a specimen and automatically prioritizing processing of the slide.

A computer-implemented method of processing an electronic image corresponding to a specimen and automatically prioritizing processing of the electronic image includes: receiving a target electronic image of a slide corresponding to a target specimen, the target specimen including a tissue sample of a patient; computing, using a machine learning system, a prioritization value of the target electronic image, the machine learning system having been generated by processing a plurality of training images, each training image including an image of human tissue and a label characterizing at least one of a slide morphology, a diagnostic value, a pathologist review outcome, and/or an analytic difficulty; and outputting a sequence of digitized pathology images, wherein a placement of the target electronic image in the sequence is based on the prioritization value of the target electronic image.

A system for processing an electronic image corresponding to a specimen and automatically prioritizing processing of the electronic image includes: at least one memory storing instructions; and at least one processor configured to execute the instructions to perform operations including: receiving a target electronic image of a slide corresponding to a target specimen, the target specimen including a tissue sample of a patient; computing, using a machine learning system, a prioritization value of the target electronic image, the machine learning system having been generated by processing a plurality of training images, each training image including an image of human tissue and a label characterizing at least one of a slide morphology, a diagnostic value, a pathologist review outcome, and/or an analytic difficulty; and outputting a sequence of digitized pathology images, wherein a placement of the target electronic image in the sequence is based on the prioritization value of the target electronic image.

A non-transitory computer-readable medium storing instructions that, when executed by at least one processor, cause the at least one processor to perform a method for processing an electronic image corresponding to a specimen and automatically prioritizing processing of the image, the method including: receiving a target electronic image of a slide corresponding to a target specimen, the target specimen including a tissue sample of a patient; computing, using a machine learning system, a prioritization value of the target electronic image, the machine learning system having been generated by processing a plurality of training images, each training image including an image of human tissue and a label characterizing at least one of a slide morphology, a diagnostic value, a pathologist review outcome, and/or an analytic difficulty; and outputting a sequence of digitized pathology images, wherein a placement of the target electronic image in the sequence is based on the prioritization value of the target electronic image.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1A:
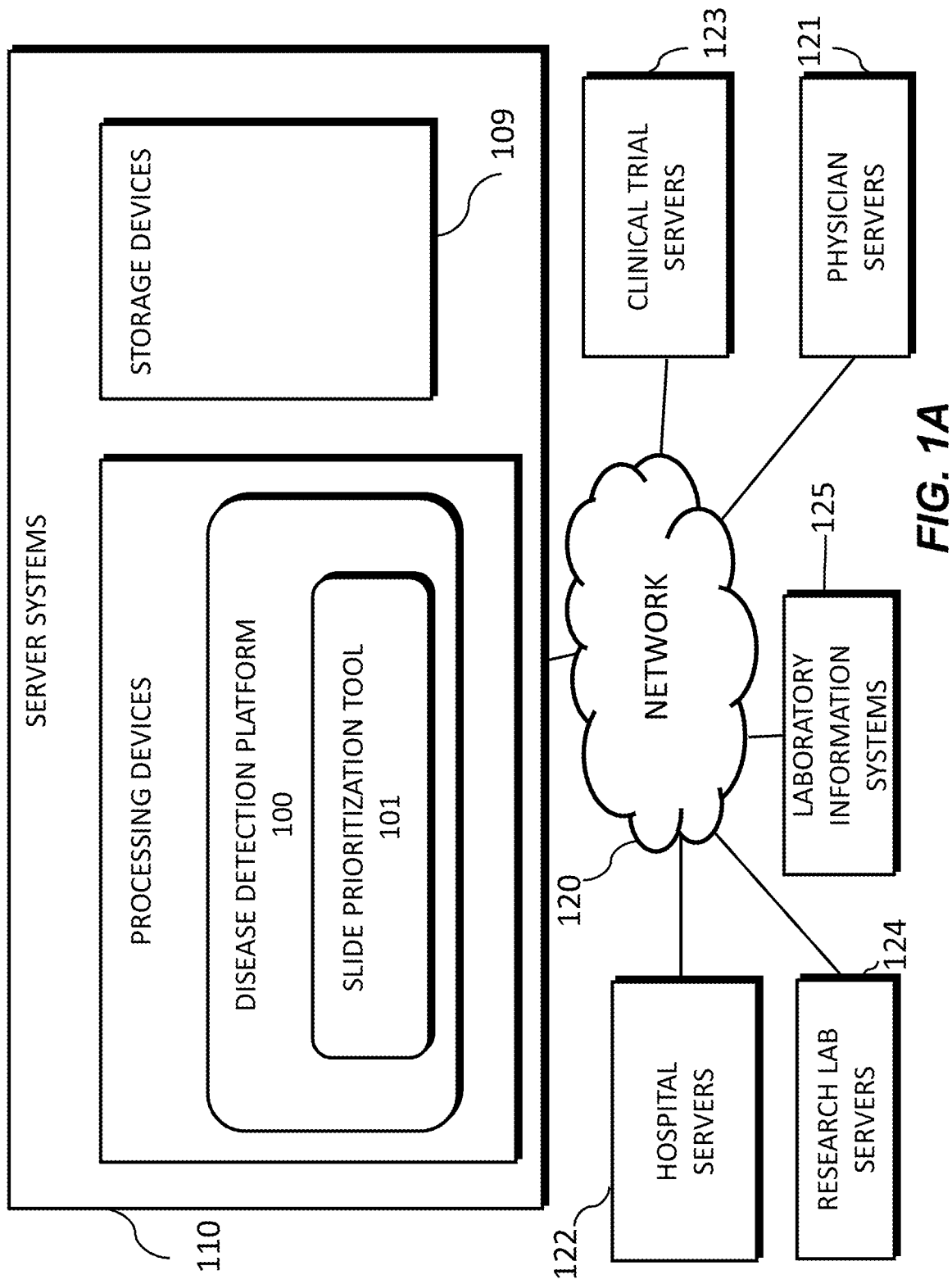
FIG. 1A is an exemplary block diagram of a system and network for providing an automatic prioritization process for preparing, processing, and reviewing images of slides of tissue specimens, according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that, unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Pathology refers to the study of diseases. More specifically, pathology refers to performing tests and analysis that are used to diagnose diseases. For example, tissue samples may be placed onto slides to be viewed under a microscope by a pathologist (e.g., a physician that is an expert at analyzing tissue samples to determine whether any abnormalities exist). That is, pathology specimens may be cut into multiple sections, stained, and prepared as slides for a pathologist to examine and render a diagnosis. When uncertain of a diagnostic finding on a slide, a pathologist may order additional cut levels, stains, or other tests to gather more information from the tissue. Technician(s) may then create new slide(s) which may contain the additional information for the pathologist to use in making a diagnosis. This process of creating additional slides may be time-consuming, not only because it may involve retrieving the block of tissue, cutting it to make a new a slide, and then staining the slide, but also because it may be batched for multiple orders. This may significantly delay the final diagnosis that the pathologist renders. In addition, even after the delay, there may still be no assurance that the new slide(s) will have information sufficient to render a diagnosis.

Pathologists may evaluate cancer and other disease pathology slides in isolation. A consolidated workflow may improve diagnosis of cancer and other diseases. The workflow may integrate, for example, slide evaluation, tasks, image analysis and cancer detection artificial intelligence (AI), annotations, consultations, and recommendations in one workstation. In particular, exemplary user interfaces may be available in the workflow, as well as AI tools that may be integrated into the workflow to expedite and improve a pathologist's work.

For example, computers may be used to analyze an image of a tissue sample to quickly identify whether additional information may be needed about a particular tissue sample, and/or to highlight to a pathologist an area in which he or she should look more closely. Thus, the process of obtaining additional stained slides and tests may be done automatically before being reviewed by a pathologist. When paired with automatic slide segmenting and staining machines, this may provide a fully automated slide preparation pipeline.

The process of using computers to assist pathologists is known as computational pathology. Computing methods used for computational pathology may include, but are not limited to, statistical analysis, autonomous or machine learning, and AI. AI may include, but is not limited to, deep learning, neural networks, classifications, clustering, and regression algorithms. By using computational pathology, lives may be saved by helping pathologists improve their diagnostic accuracy, reliability, efficiency, and accessibility. For example, computational pathology may be used to assist with detecting slides suspicious for cancer, thereby allowing pathologists to check and confirm their initial assessments before rendering a final diagnosis.

Histopathology refers to the study of a specimen that has been placed onto a slide. For example, a digital pathology image may be comprised of a digitized image of a microscope slide containing the specimen (e.g., a smear). One method a pathologist may use to analyze an image on a slide is to identify nuclei and classify whether a nucleus is normal (e.g., benign) or abnormal (e.g., malignant). To assist pathologists in identifying and classifying nuclei, histological stains may be used to make cells visible. Many dye-based staining systems have been developed, including periodic acid-Schiff reaction, Masson's trichrome, nissl and methylene blue, and Haemotoxylin and Eosin (H&E). For medical diagnosis, H&E is a widely used dye-based method, with hematoxylin staining cell nuclei blue, eosin staining cytoplasm and extracellular matrix pink, and other tissue regions taking on variations of these colors. In many cases, however, H&E-stained histologic preparations do not provide sufficient information for a pathologist to visually identify biomarkers that can aid diagnosis or guide treatment. In this situation, techniques such as immunohistochemistry (IHC), immunofluorescence, in situ hybridization (ISH), or fluorescence in situ hybridization (FISH), may be used. IHC and immunofluorescence involve, for example, using antibodies that bind to specific antigens in tissues enabling the visual detection of cells expressing specific proteins of interest, which can reveal biomarkers that are not reliably identifiable to trained pathologists based on the analysis of H&E stained slides. ISH and FISH may be employed to assess the number of copies of genes or the abundance of specific RNA molecules, depending on the type of probes employed (e.g. DNA probes for gene copy number and RNA probes for the assessment of RNA expression). If these methods also fail to provide sufficient information to detect some biomarkers, genetic testing of the tissue may be used to confirm if a biomarker is present (e.g., overexpression of a specific protein or gene product in a tumor, amplification of a given gene in a cancer).

A digitized image may be prepared to show a stained microscope slide, which may allow a pathologist to manually view the image on a slide and estimate a number of stained abnormal cells in the image. However, this process may be time consuming and may lead to errors in identifying abnormalities because some abnormalities are difficult to detect. Computational processes and devices may be used to assist pathologists in detecting abnormalities that may otherwise be difficult to detect. For example, AI may be used to predict biomarkers (such as the overexpression of a protein and/or gene product, amplification, or mutations of specific genes) from salient regions within digital images of tissues stained using H&E and other dye-based methods. The images of the tissues could be whole slide images (WSI), images of tissue cores within microarrays or selected areas of interest within a tissue section. Using staining methods like H&E, these biomarkers may be difficult for humans to visually detect or quantify without the aid of additional testing. Using AI to infer these biomarkers from digital images of tissues has the potential to improve patient care, while also being faster and less expensive.

The detected biomarkers or the image alone could then be used to recommend specific cancer drugs or drug combination therapies to be used to treat a patient, and the AI could identify which drugs or drug combinations are unlikely to be successful by correlating the detected biomarkers with a database of treatment options. This can be used to facilitate the automatic recommendation of immunotherapy drugs to target a patient's specific cancer. Further, this could be used for enabling personalized cancer treatment for specific subsets of patients and/or rarer cancer types.

In the field of pathology, it may be difficult to provide systematic quality control ("QC"), with respect to pathology specimen preparation, and quality assurance ("QA") with respect to the quality of diagnoses, throughout the histopathology workflow. Systematic quality assurance is difficult because it is resource and time intensive as it may require duplicative efforts by two pathologists. Some methods for quality assurance include (1) second review of first-time diagnosis cancer cases; (2) periodic reviews of discordant or changed diagnoses by a quality assurance committee; and/or (3) random review of a subset of cases. These are non-exhaustive, mostly retrospective, and manual. With an automated and systematic QC and QA mechanism, quality can be ensured throughout the workflow for every case. Laboratory quality control and digital pathology quality control are critical to the successful intake, process, diagnosis, and archive of patient specimens. Manual and sampled approaches to QC and QA confer substantial benefits. Systematic QC and QA has the potential to provide efficiencies and improve diagnostic quality.

As described above, example embodiments described herein provide an integrated platform allowing a fully automated process including data ingestion, processing and viewing of digital pathology images via a web-browser or other user interface, while integrating with a laboratory information system (LIS). Further, clinical information may be aggregated using cloud-based data analysis of patient data. The data may come from hospitals, clinics, field researchers, etc., and may be analyzed by machine learning, computer vision, natural language processing, and/or statistical algorithms to do real-time monitoring and forecasting of health patterns at multiple geographic specificity levels.

Previously, there was no way of prioritizing the production or analysis of pathology slides. Accordingly, example embodiments described herein automatically prioritize slide preparation, processing, and review, in order to streamline and speed digitized pathology image-based diagnoses.

This automation has, at least, the benefits of (1) minimizing the amount of time wasted by a pathologist determining a slide to be insufficient to make a diagnosis, (2) minimizing the time (e.g., average total time) from specimen acquisition to diagnosis by avoiding the additional time between when additional tests are ordered and when they are produced, (3) allowing higher volumes of slides to be processed or reviewed by a pathologist in a shorter amount of time, (4) contributing to more informed/precise diagnoses by reducing the overhead of requesting additional testing for a pathologist, (5) identifying or verifying correct properties (e.g., pertaining to a specimen type) of a digital pathology image, and/or (6) training pathologists, etc. The present disclosure uses automated detection, prioritization and triage of all pathology cases to a clinical digital workflow involving digitized pathology slides, such that pathology slide analysis may be prioritized before diagnostic review by a pathologist. For example, the disclosed embodiments may provide case-level prioritization, and prioritize slides with significant findings within each case. These prioritization embodiments may make digital review of pathology slides more efficient in various settings (e.g., academic, commercial lab, hospital, etc.).

Exemplary global outputs of the disclosed embodiments may contain information or slide parameter(s) about an entire image or slide, e.g., the depicted specimen type, the overall quality of the cut of the specimen of the slide, the overall quality of the glass pathology slide itself, or tissue morphology characteristics. Exemplary local outputs may indicate information in specific regions of an image or slide, e.g., a particular slide region may be labeled as blurred or containing an irrelevant specimen. The present disclosure includes embodiments for both developing and using the disclosed automatic prioritization process for slide preparation, processing, and review, as described in further detail below.

FIG. 1A illustrates a block diagram of a system and network for providing an automatic prioritization process for preparing, processing, and reviewing images of slides of tissue specimens, using machine learning, according to an exemplary embodiment of the present disclosure.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an exemplary embodiment of the present application, the electronic network 120 may also be connected to server systems 110, which may include processing devices that are configured to implement a disease detection platform 100, which includes a slide prioritization tool 101 for providing an automatic prioritization process for preparing, processing, and reviewing images of slides of tissue specimens, according to an exemplary embodiment of the present disclosure.

The physician servers 121, hospital servers 122, clinical trial servers 123, research lab servers 124, and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server system(s) 110 may include one or more storage devices 109 for storing images and data received from at least one of the physician servers 121, hospital servers 122, clinical trial servers 123, research lab servers 124, and/or laboratory information systems (LIS) 125. Server systems 110 may also include processing devices for processing images and data stored in the storage devices 109. Server systems 110 may further include one or more machine learning tool(s) or capabilities. For example, the processing devices may include a machine learning tool for a disease detection platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or LIS 125 refer to systems used by pathologists for reviewing the images of the slides. In hospital settings, tissue type information may be stored in a LIS 125. According to an exemplary embodiment of the present disclosure, slides may be automatically prioritized without needing to access the LIS 125. For example, a third party may be given anonymized access to the image content without the corresponding specimen type label stored in the LIS. Additionally, access to LIS content may be limited due to its sensitive content.

Figure 1B:
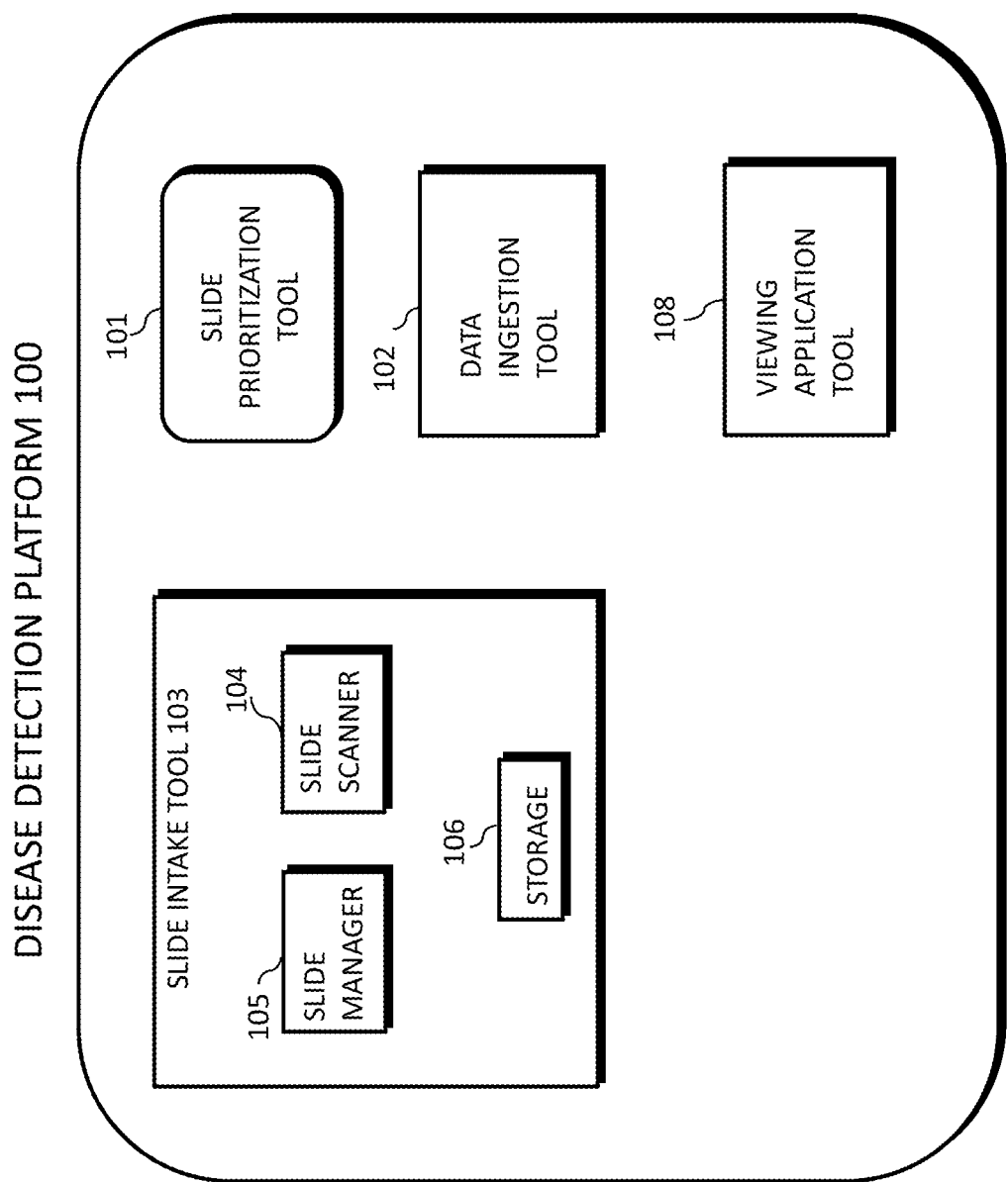
FIG. 1B is an exemplary block diagram of a disease detection platform 100, according to an exemplary embodiment of the present disclosure.

FIG. 1B illustrates an exemplary block diagram of a disease detection platform 100 for providing an automatic prioritization process for preparing, processing, and reviewing images of slides of tissue specimens, using machine learning.

Specifically, FIG. 1B depicts components of the disease detection platform 100, according to one embodiment. For example, the disease detection platform 100 may include a slide prioritization tool 101, a data ingestion tool 102, a slide intake tool 103, a slide scanner 104, a slide manager 105, a storage 106, and a viewing application tool 108.

The slide prioritization tool 101, as described below, refers to a process and system for providing an automatic prioritization process for preparing, processing, and reviewing images of slides of tissue specimens, according to an exemplary embodiment.

The data ingestion tool 102 refers to a process and system for facilitating a transfer of the digital pathology images to the various tools, modules, components, and devices that are used for classifying and processing the digital pathology images, according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images on the slides into digitized pathology images and store the digitized images in storage 106.

The viewing application tool 108 refers to a process and system for providing a user (e.g., pathologist) with specimen property or image property information pertaining to digital pathology image(s), according to an exemplary embodiment. The information may be provided through various output interfaces (e.g., a screen, a monitor, a storage device, and/or a web browser, etc.).

The slide prioritization tool 101, and each of its components, may transmit and/or receive digitized slide images and/or patient information to server systems 110, physician servers 121, hospital servers 122, clinical trial servers 123, research lab servers 124, and/or laboratory information systems 125 over a network 120. Further, server systems 110 may include storage devices for storing images and data received from at least one of the slide prioritization tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

Any of the above devices, tools, and modules may be located on a device that may be connected to an electronic network 120, such as the Internet or a cloud service provider, through one or more computers, servers, and/or handheld mobile devices.

Figure 1C:
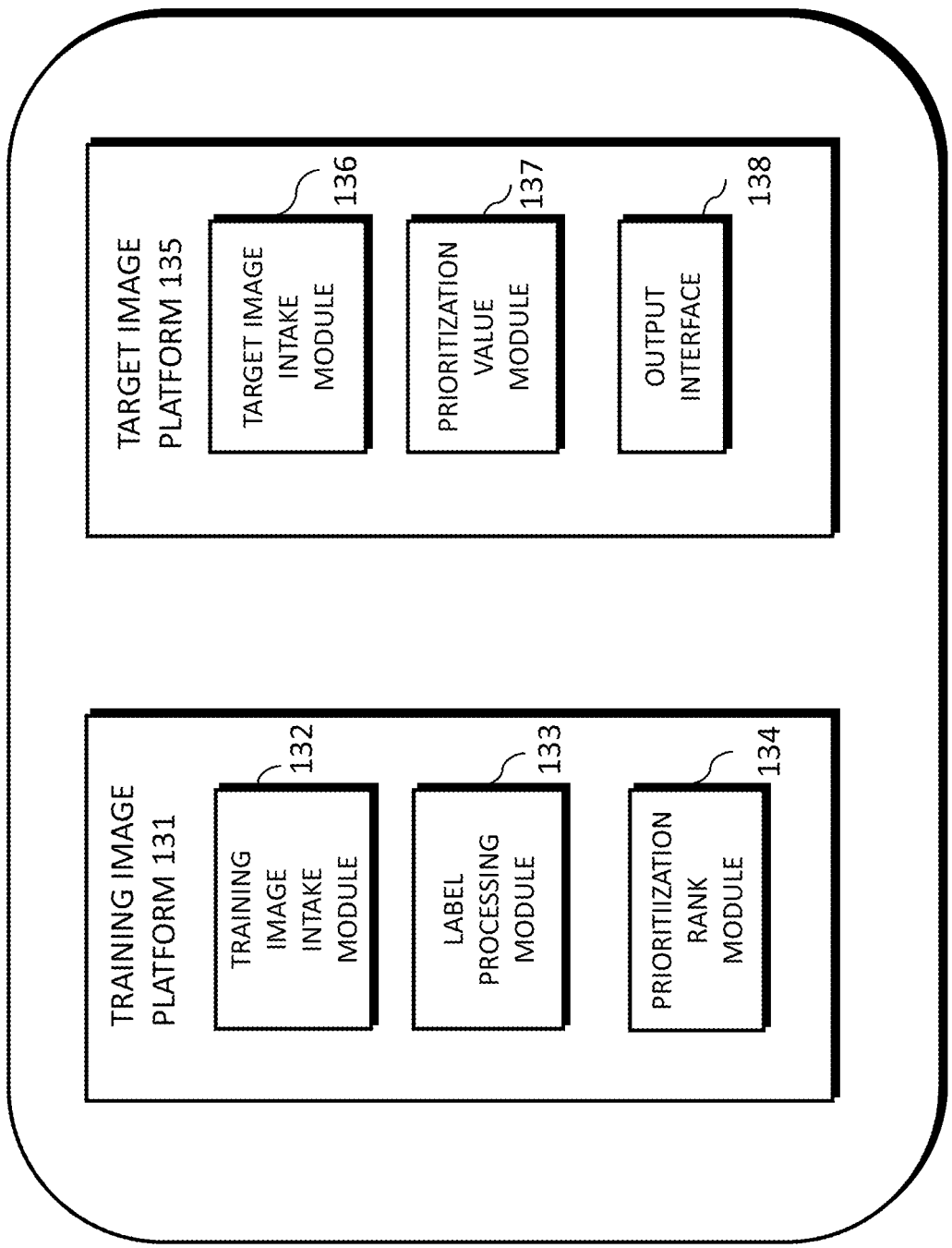
FIG. 1C is an exemplary block diagram of a slide prioritization tool 101, according to an exemplary embodiment of the present disclosure.

FIG. 1C illustrates an exemplary block diagram of a slide prioritization tool 101, according to an exemplary embodiment of the present disclosure. The slide prioritization tool 101 may include a training image platform 131 and/or a target image platform 135.

The training image platform 131 may include a training image intake module 132, a label processing module 133, and/or a prioritization rank module 134.

The training image platform 131 may create or receive training images that are used to train a machine learning model and/or system to effectively analyze and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized tissue samples from a 3D imaging device, such as microCT.

The training image intake module 132 may create or receive a dataset comprising one or more training images corresponding to images of a human tissue and/or images that are graphically rendered. For example, the training images may be received from any one or any combination of the server systems 110, physician servers 121, hospital servers 122, clinical trial servers 123, research lab servers 124, and/or laboratory information systems 125. This dataset may be kept on a digital storage device. The label processing module 133 may, for each training image, determine a label characterizing at least one of a slide morphology, a diagnostic value, a pathologist review outcome, and/or an analytic difficulty. The prioritization rank module 134 may process images of tissues and determine a predicted prioritization rank for each training image.

According to one embodiment, the target image platform 135 may include a target image intake module 136, a prioritization value module 137, and an output interface 138. The target image platform 135 may receive a target image and apply the machine learning model to the target image to compute a prioritization value for the target image. For example, the target image may be received from any one or any combination of the server systems 110, physician servers 121, hospital servers 122, clinical trial servers 123, research lab servers 124, and/or laboratory information systems 125. The target image intake module 136 may receive a target image corresponding to a target specimen. The prioritization value module 137 may apply the machine learning model to the target image to compute a prioritization value for the target image.

The output interface 138 may be used to output information about the target image and the target specimen. (e.g., to a screen, monitor, storage device, web browser, etc.).

Figure 1D:
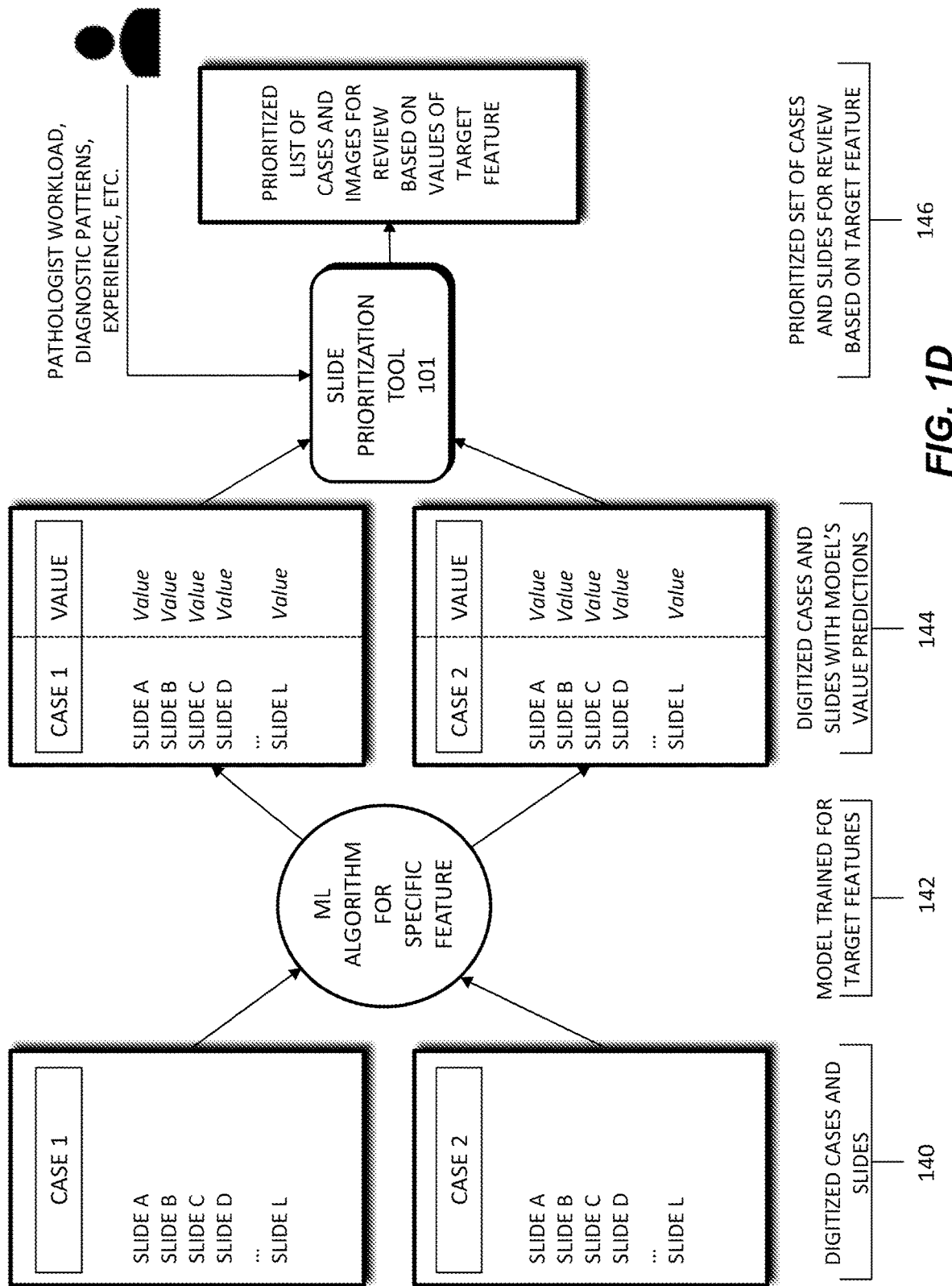
FIG. 1D is a diagram of an exemplary system for an automatic prioritization process for pathology slide preparation, processing, and review, according to an exemplary embodiment of the present disclosure.

FIG. 1D depicts a schematic diagram of an exemplary system and workflow for prioritizing slides in a digital pathology workflow. In this workflow, a machine learning model 142 may receive digitized cases and slides 140 as input. The digitized cases and slides 140 may be comprised of images of a patient's pathology slides and/or electronic data regarding patient characteristics, treatment history, patient context, slide data, etc. Patient characteristics may include a patient's age, height, body weight, family medical history, allergies, etc. Treatment history may include tests performed on a patient, past procedures performed on a patient, radiation exposure of a patient, etc. Case context may refer to whether a case/slide is part of a clinical study, experimental treatment, follow-up report, etc. Slide data may include stain(s) performed, location of tissue slice, time/date at which a slide was made, lab making the slide, etc.

The machine learning model 142 may be trained using the digitized cases and slides 140. The trained machine learning model 142 may output one or more prioritization value predictions 144. For example, the trained machine learning model 142 may generate a prioritization value 144 for a selected digitized case/slide. The selected digitized case/slide may be a new or additional case/slide, not included in the input digitized cases and slides 140. Alternately, machine learning model 142 may also be used to output a prioritization value for a selected digitized case/slide that was part of the digitized cases and slides 140.

A prioritization order 146 may be generated based on the generated prioritization value 144. For example, a prioritization value 144 may be output by the machine learning model 142, for each case/slide in a set of cases/slides. The prioritization order 146 may then be comprised of a listing, or docket, of cases for a pathologist to review, where the cases are listed in an order based on each case's prioritization value 144. This prioritization of cases may allow a pathologist to triage their cases and review cases of higher urgency or priority first. In some cases, the prioritization order 146 may be adjusted, prior to a pathologist's review. For example, a prioritization value 144 of a case may increase if a case has been in queue past a certain amount of time, or if additional information is received on the case. The methods of FIG. 1D are described in further detail below.

Figure 2:
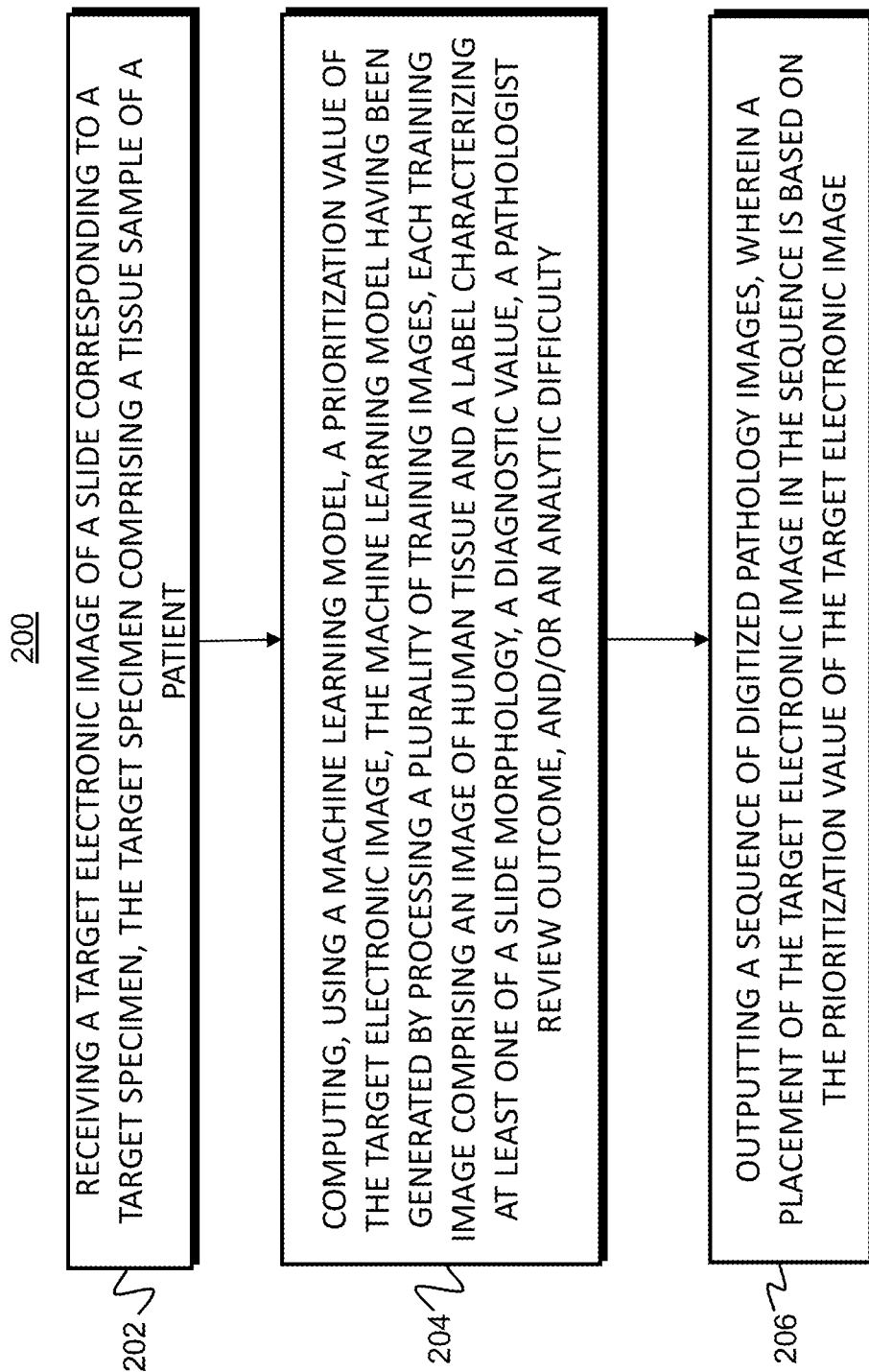
FIG. 2 is a flowchart of an exemplary method for analyzing an image of a slide corresponding to a specimen and providing automatically prioritized processing of the slide, using machine learning, according to an exemplary embodiment of the present disclosure.

FIG. 2 is a flowchart illustrating an exemplary method of a tool for processing an image of a slide corresponding to a specimen and automatically prioritizing processing of the slide, according to an exemplary embodiment of the present disclosure. For example, an exemplary method 200 (e.g., steps 202 to 206) may be performed by the slide prioritization tool 101 automatically or in response to a request from a user (e.g., physician, pathologist, etc.).

According to one embodiment, the exemplary method 200 for automatically prioritizing processing of the slide may include one or more of the following steps. In step 202, the method may include receiving a target image of a slide corresponding to a target specimen, the target specimen comprising a tissue sample of a patient. For example, the target image may be received from any one or any combination of the server systems 110, physician servers 121, hospital servers 122, clinical trial servers 123, research lab servers 124, and/or laboratory information systems 125.

In step 204, the method may include computing, using a machine learning model, a prioritization value of the target image, the machine learning model having been generated by processing a plurality of training images, each training image comprising an image of human tissue and a label characterizing at least one of a slide morphology, a diagnostic value, a pathologist review outcome, and/or an analytic difficulty. The label may include a preparation value corresponding to a likelihood that further preparation is to be performed for the target image. Further preparation may be performed for the target image based on at least one of a specimen recut, an immunohistochemical stain, additional diagnostic testing, additional consultation, and/or a special stain. The label may include a diagnostic feature of the target image, the diagnostic feature comprising at least one of cancer presence, cancer grade, treatment effects, precancerous lesions, and/or presence of infectious organisms. The prioritization value of the target image may include a first prioritization value of the target image for a first user and a second prioritization value of the target image for a second user, the first prioritization value may be determined based on the first user's preferences and the second prioritization value may be determined based on the second user's preferences. The label may include an artifact label corresponding to at least one of scanning lines, missing tissue, and/or blur.

The training images may be received from any one or any combination of the server systems 110, physician servers 121, hospital servers 122, clinical trial servers 123, research lab servers 124, and/or laboratory information systems 125. This dataset may be kept on a digital storage device. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to)

H&E, Hematoxylin alone, IHC, molecular pathology, etc.; and/or (b) digitized tissue samples from a 3D imaging device, such as microCT.

In step 206, the method may include outputting a sequence of digitized pathology images, and a placement of the target image in the sequence is based on the prioritization value of the target image.

Different methods for implementing machine learning algorithms and/or architectures may include but are not limited to (1) CNN (Convolutional Neural Network); (2) MIL (Multiple Instance Learning); (3) RNN (Recurrent Neural Network); (4) Feature aggregation via CNN; and/or (5) Feature extraction following by ensemble methods (e.g., random forest), linear/non-linear classifiers (e.g., SVMs (support vector machines), MLP (multiplayer perceptron), and/or dimensionality reduction techniques (e.g., PCA (principal component analysis), LDA (linear discriminant analysis), etc.). Example features may include vector embeddings from a CNN, single/multi-class output from a CNN, and/or multi-dimensional output from a CNN (e.g., a mask overlay of the original image). A CNN may learn feature representations for classification tasks directly from pixels, which may lead to better diagnostic performance. When detailed annotations for regions or pixel-wise labels are available, a CNN may be trained directly if there is a large amount of labeled data. However, when labels are only at the whole slide level or over a collection of slides in a group (which may be called a "part" in pathology), MIL may be used to train the CNN or another neural network classifier, where MIL learns the image regions that are diagnostic for the classification task leading to the ability to learn without exhaustive annotations. An RNN may be used on features extracted from multiple image regions (e.g., tiles) that it then processes to make a prediction. Other machine learning methods, e.g., random forest, SVM, and numerous others may be used with either features learned by a CNN, a CNN with MIL, or using hand-crafted image features (e.g., SIFT or SURF) to do the classification task, but they may perform poorly when trained directly from pixels. These methods may perform poorly compared to CNN-based systems when there is a large amount of annotated training data available. Dimensionality reduction techniques could be used as a pre-processing step before using any of the classifiers mentioned, which could be useful if there was little data available.

According to one or more embodiments, any of the above algorithms, architectures, methodologies, attributes, and/or features may be combined with any or all of the other algorithms, architectures, methodologies, attributes, and/or features. For example, any of the machine learning algorithms and/or architectures (e.g., neural network methods, convolutional neural networks (CNNs), recurrent neural networks (RNNs), etc.) may be trained with any of the training methodologies (e.g., Multiple Instance Learning, Reinforcement Learning, Active Learning, etc.)

The description of the terms below is merely exemplary and is not intended to limit the terms in any way.

A label may refer to information about an input to a machine learning algorithm that the algorithm is attempting to predict.

For a given image of size N×M, a segmentation may be another image of size N×M that, for each pixel in an original image, assigns a number that describes the class or type of that pixel. For example, in a WSI, elements in the mask may categorize each pixel in the input image as belonging to the classes of, e.g., background, tissue and/or unknown.

Slide level information may refer to information about a slide in general, but not necessarily a specific location of that information in the slide.

A heuristic may refer to a logic rule or function that deterministically produces an output, given inputs. For example: if a prediction that a slide should be prioritized over another slide is greater than or equal to 32%, then output one, if not, output 0.

Embedding may refer to a conceptual high-dimensional numerical representation of low-dimensional data. For example, if a WSI is passed through a CNN training to classify tissue type, the numbers on the last layer of the network may provide an array of numbers (e.g., in the order of thousands) that contain information about the slide (e.g., information about a type of tissue).

Slide level prediction may refer to a concrete prediction about a slide as a whole. For example, a slide level prediction may be that the slide should be prioritized over another slide. Further, slide level prediction may refer to individual probability predictions over a set of defined classes.

A classifier may refer to a model that is trained to take input data and associate it with a category.

According to one or more embodiments, the machine learning model may be trained in different ways. For example, the training of the machine learning model may be performed by any one or any combination of supervised training, semi-supervised training, unsupervised training classifier training, mixed training, and/or uncertainty estimation. The type of training used may depend on an amount of data, a type of data, and/or a quality of data. Table 1 below describes a non-limiting list of some types of training and the corresponding features.

TABLE 1

| Index | Input | Label | Model | Output |
|---|---|---|---|---|
| 1 | WSI Embedding | Segmentation | CNN, RNN, MLP | Predicted Segmentation Embedding |
| 2 | WSI Embedding | Slide Level Information | CNN, RNN, MLP | Embedding Slide level prediction |
| 3 | WSI Embedding | — | CNN, RNN, MLP | Embedding |
| 4 | Embedding | Slide Level Information | SVM, MLP, RNN, Random Forests | Slide level prediction |
| 5 | Slide level prediction | Measure of how wrong the prediction was | MLP, RNN, Statistical Model | Predict a likelihood that an original prediction is wrong |

Supervised training may be used with a small amount of data to provide a seed for a machine learning model. In supervised training, the machine learning model may look for a specific item (e.g., bubbles, tissue folds, etc.), flag the slide, and quantify how much of the specific item is present in the slide.

According to one embodiment, an example fully supervised training may take as an input a WSI and may include a label of segmentation. Pipelines for a fully supervised training may include (1) 1; (2) 1, Heuristic; (3) 1, 4, Heuristic; (4) 1, 4, 5, Heuristic; and/or (5) 1, 5, Heuristic. Advantages of a fully supervised training may be that (1) it may require fewer slides and/or (2) the output is explainable because (a) it may be known which areas of the image contributed to the diagnosis; and (b) it may be known why a slide is prioritized over another (e.g., a diagnostic value, an analytic difficulty, etc.). A disadvantage of using a fully supervised training may be that it may require large amounts of segmentation which may be difficult to acquire.

According to one embodiment, an example semi-supervised (e.g., weakly supervised) training may take as an input WSI and may include a label of slide level information. Pipelines for a semi-supervised training may include (1) 2; (2) 2, Heuristic; (3) 2, 4, Heuristic; (4) 2, 4, 5, Heuristic; and/or (5) 2, 5, Heuristic. Advantages of using a semi-supervised training may be that (1) the types of labels required may be present in many hospital records; and (2) output is explainable because (a) it may be known which areas of the image contributed most to the diagnosis; and (b) it may be known why a slide was prioritized over another (e.g., a diagnostic value, an analytic difficulty, etc.). A disadvantage of using a semi-supervised training is that it may be difficult to train. For example, the model may need to use a training scheme such as Multiple Instance Learning, Activate Learning, and/or distributed training to account for the fact that there is limited information about where in the slide the information is that should lead to a decision.

According to one embodiment, an example unsupervised training may take as an input a WSI and may require no label. The pipelines for an unsupervised training may include (1) 3, 4; and/or (2) 3, 4, Heuristic. An advantage of unsupervised training may be that it does not require any labels. Disadvantages of using an unsupervised training may be that (1) it may be difficult to train. For example, it may need to use a training scheme such as Multiple Instance Learning, Activate Learning, and/or distributed training to account for the fact that there is limited information about where in the slide the information is that should lead to a decision; (2) it may require additional slides; and/or (3) it may be less explainable because it might output a prediction and probability without explaining why that prediction was made.

According to one embodiment, an example mixed training may include training any of the example pipelines described above for fully supervised training, semi-supervised training, and/or unsupervised training, and then use the resulting model as an initial point for any of the training methods. Advantages of mixed training may be that (1) it may require less data; (2) it may have improved performance; and/or (3) it may allow a mixture of different levels of labels (e.g., segmentation, slide level information, no information). Disadvantages of mixed training may be that (1) it may be more complicated and/or expensive to train; and/or (2) it may require more code that may increase a number and complexity of potential bugs.

According to one embodiment, an example uncertainty estimation may include training any of the example pipelines described above for fully supervised training, semi-supervised training, and/or unsupervised training, for any task related to slide data using uncertainty estimation in the end of the pipeline. Further, a heuristic or classifier may be used to predict whether a slide should be prioritized over another based on an amount of uncertainty in the prediction of the test. An advantage of uncertainty estimation may be that it is robust to out-of-distribution data. For example, when unfamiliar data is presented, it may still correctly predict that it is uncertain. Disadvantages of uncertainty estimation may be that (1) it may need more data; (2) it may have poor overall performance; and/or (3) it may be less explainable because the model might not necessarily identify how a slide or slide embedding is abnormal.

According to one embodiment, an ensembles training may include simultaneously running models produced by any of the example pipelines described above, and combining the outputs by a heuristic or a classifier to produce robust and accurate results. Advantages of ensembles training may be that (1) it is robust to out-of-distribution data; and/or (2) it may combine advantages and disadvantages of other models, resulting in a minimization of disadvantages (e.g., a supervised training model combined with an uncertainty estimation model, and a heuristic that uses a supervised model when incoming data is in distribution and uses an uncertainty model when data is out of distribution, etc.). Disadvantages of ensembles training may be that (1) it may be more complex; and/or (2) it may be expensive to train and run.

Training techniques discussed herein may also proceed in stages, where images with greater annotations are initially used for training, which may allow for more effective later training using slides that have fewer annotations, are less supervised, etc.

Training may begin using the slides that are the most thoroughly annotated, relative to all the training slide images that may be used. For example, training may begin using supervised learning. A first set of slides images may be received or determined with associated annotations. Each slide may have marked and/or masked regions and may include information such as whether the slide should be prioritized over another. The first set of slides may be provided to a training algorithm, for example a CNN, which may determine correlations between the first set of slides and their associated annotations.

After training with the first set of images is completed, a second set of slide images may be received or determined having fewer annotations than the first set, for example with partial annotations. In one embodiment, the annotations might only indicate that the slide has a diagnosis or quality issue associated with it, but might not specify what or where disease may be found, etc. The second set of slide images may be trained using a different training algorithm than the first, for example Multiple Instance Learning. The first set of training data may be used to partially train the system, and may make the second training round more effective at producing an accurate algorithm.

In this way, training may proceed in any number of stages, using any number of algorithms, based on the quality and types of the training slide images. These techniques may be utilized in a situations where multiple training sets of images are received, which may be of varying quality, annotation levels, and/or annotation types.

Figure 3:
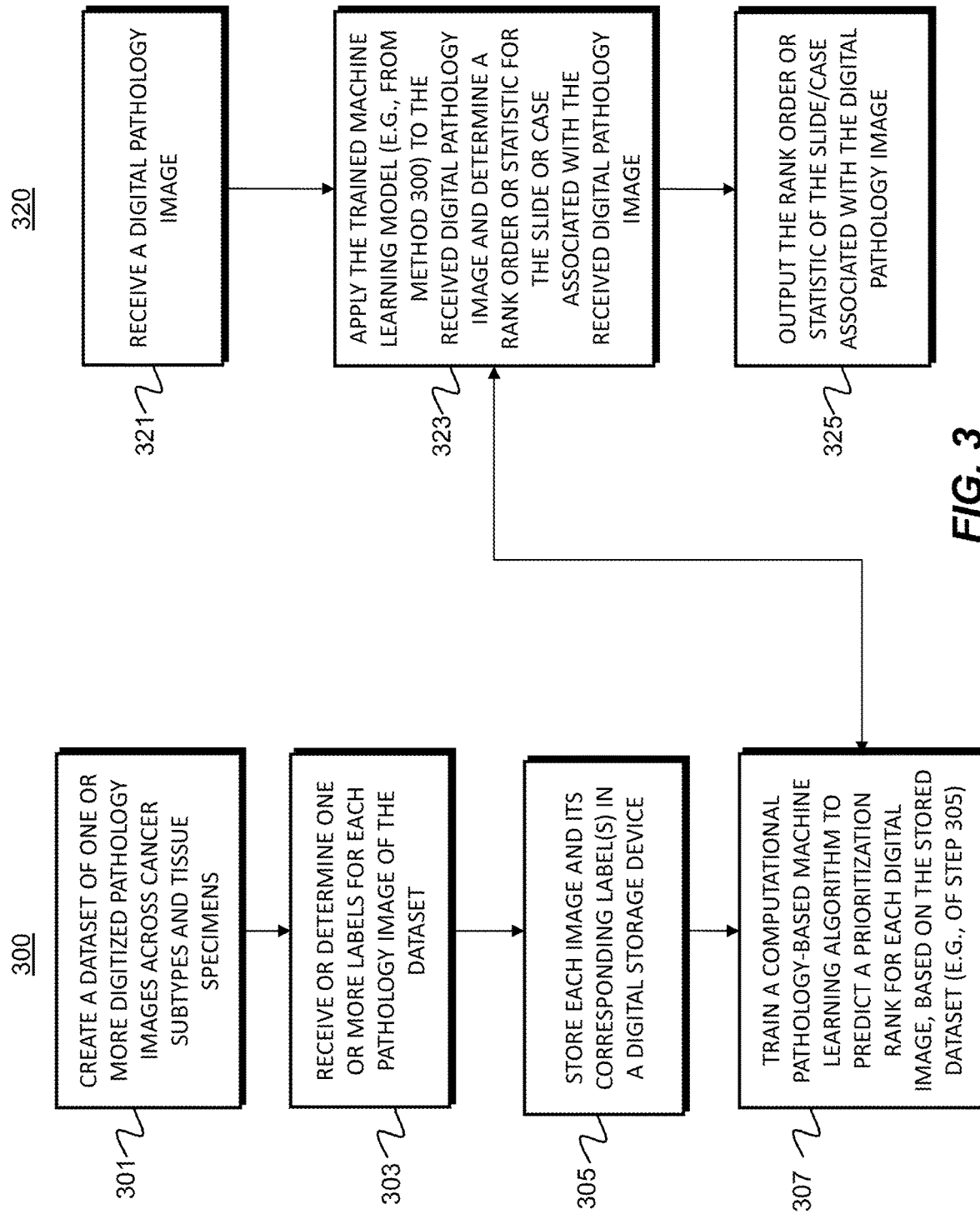
FIG. 3 is a flowchart of an exemplary embodiment for automatically prioritizing pathology slide preparation, processing, and review, according to an exemplary embodiment of the present disclosure.

FIG. 3 illustrates exemplary methods for determining an order in which to analyze a plurality of pathology slides. For example, exemplary methods 300 and 320 (e.g., steps 301-325) may be performed by the slide prioritization tool 101 automatically or in response to a request from a user (e.g., physician, pathologist, etc.).

According to one embodiment, the exemplary method 300 for determining an order in which to analyze a plurality of pathology slides may include one or more of the steps below. In step 301, the method may include creating a dataset of one or more digitized pathology images across cancer subtypes and tissue specimens (e.g., histology, cytology, hematology, microCT, etc.). In step 303, the method may include receiving or determining one or more labels (e.g., slide morphology, diagnostic, outcome, difficulty, etc.) for each pathology image of the dataset. In step 305, the method may include storing each image and its corresponding label(s) in a digital storage device (e.g., hard drive, network drive, cloud storage, RAM, etc.)

In step 307, the method may include training a computational pathology-based machine learning algorithm that takes, as input, one or more digital images of a pathology specimen, and predicting a prioritization rank for each digital image. Different methods for implementing the machine learning algorithm may include but are not limited to (1) CNN (Convolutional Neural Network); (2) MIL (Multiple Instance Learning); (3) RNN (Recurrent Neural Network); (4) Feature aggregation via CNN; and/or (5) Feature extraction following by ensemble methods (e.g., random forest), linear/non-linear classifiers (e.g., SVMs, MLP), and/or dimensionality reduction techniques (e.g., PCA, LDA). Example features may include vector embeddings from a CNN, single/multi-class output from a CNN, and/or multi-dimensional output from a CNN (e.g., a mask overlay of the original image). A CNN may learn feature representations for classification tasks directly from pixels, which may lead to better diagnostic performance. When detailed annotations for regions or pixel-wise labels are available, a CNN may be trained directly if there is a large amount of labeled data. However, when labels are only at the whole slide level or over a collection of slides in a group (which may be called a "part" in pathology), MIL may be used to train the CNN or another neural network classifier, where MIL learns the image regions that are diagnostic for the classification task leading to the ability to learn without exhaustive annotations. An RNN may be used on features extracted from multiple image regions (e.g., tiles) that it then processes to make a prediction. Other machine learning methods, e.g., random forest, SVM, and numerous others may be used with either features learned by a CNN, a CNN with MIL, or using hand-crafted image features (e.g., SIFT or SURF) to do the classification task, but they may perform poorly when trained directly from pixels. These methods tend to perform poorly compared to CNN-based systems when there is a large amount of annotated training data available. Dimensionality reduction techniques could be used as a pre-processing step before using any of the classifiers mentioned, which could be useful if there was little data available.

The above description of machine learning algorithms for FIG. 2 (e.g., Table 1 and corresponding description) may also apply to the machine learning algorithms of FIG. 3.

An exemplary method 320 for using the slide prioritization tool may include one or more of the steps below. In step 321, the method may include receiving a digital pathology image corresponding to a user. In step 323, the method may include determining a rank order or statistic for a slide and/or a case associated with the received digital pathology image. The rank order or statistic may be determined by applying the trained computational pathology-machine learning algorithm (e.g., of method 300) to the received image. The rank order or statistic may be used to prioritize review or additional slide preparation for the slide associated with the received image or the case associated with the received image.

In step 325, the method may include outputting the rank order or statistic. One output may include a determination and/or display of one or more variation(s) in order, based on preferences, heuristics, statistics, objectives of user (e.g., efficiency, difficulty, urgency, etc.). Alternately or in addition, an output may include a visual sorting of the received image at a case level, based on the generated order. For example, such visual sorting may include a display comprising a sorting of cases ordered based on maximum or minimum slide probability for a target feature, based on an average probability across all slides for a target feature, based on the raw number of slides showing a target feature, etc. Yet another output may include a visualization of a sorting at the slide level or tissue block level within each case, based on the generated order. The visual sorting may be performed by a user, and/or computationally.

The above-described slide prioritization tool may include particular applications or embodiments usable in research, and/or production/clinical/industrial settings. The embodiments may occur at various phases of development and use. A tool may employ one or more of the embodiments below.

According to one embodiment, a prioritization may be based on quality control. Quality control issues may impact a pathologist's ability to render a diagnosis. In other words, quality control issues may increase the turnaround time for a case. For example, a poorly prepared and scanned slide may be sent to a pathologist's queue, before a quality control issue is found. According to one embodiment, the turnaround time may be shortened by identifying a quality control issue before it reaches a pathologist's queue, therefore saving time in a pathology diagnosis workflow. For example, the present embodiment may identify and triage cases/slide(s) with quality control issues and signal the issue to lab and scanner technicians, before the slide(s) reach a pathologist. This quality control catch earlier in the workflow may improve efficiency.

Figure 4:
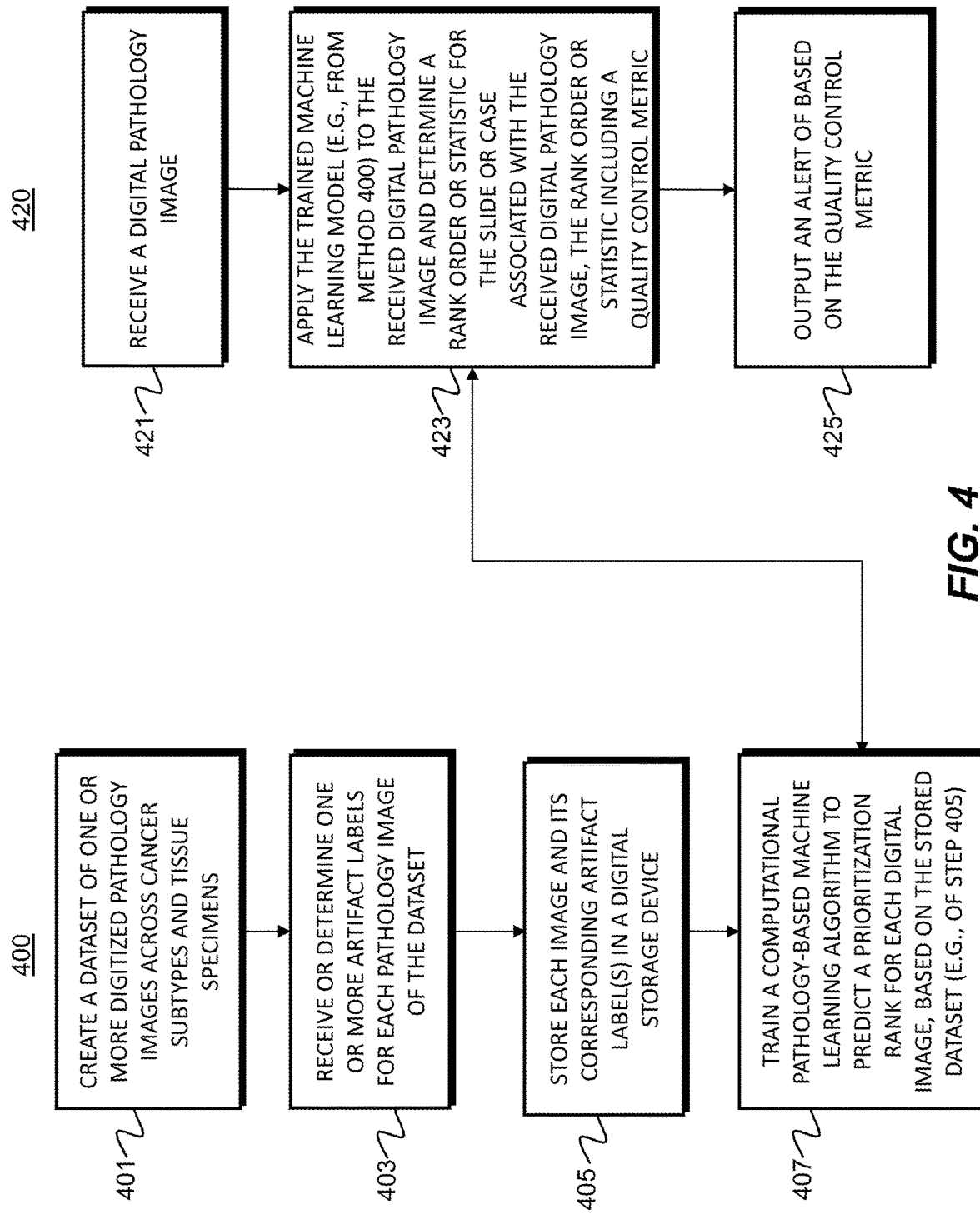
FIG. 4 is a flowchart of an exemplary embodiment of generating and using a quality control-based pathology slide preparation prioritization tool, according to an exemplary embodiment of the present disclosure.

FIG. 4 illustrates exemplary methods for developing a quality control prioritization tool. For example, exemplary methods 400 and 420 (e.g., steps 401-425) may be performed by the slide prioritization tool 101 automatically or in response to a request from a user (e.g., physician, pathologist, etc.).

According to one embodiment, the exemplary method 400 for developing a quality control prioritization tool may include one or more of the steps below. In step 401, the method may include creating a dataset of digitized pathology images across cancer subtypes and tissue specimens (e.g., histology, cytology, hematology, microCT, etc.). In step 403, the method may include receiving or determining one or more labels (e.g., slide morphology, diagnostic, outcome, difficulty, etc.) for each pathology image of the dataset. Additional exemplary labels may include but are not limited to scanning artifacts (e.g., scanning lines, missing tissue, blur, etc.) and slide preparation artifacts (e.g., folded tissue, poor staining, damaged slide, marking, etc.). In step 405, the method may include storing each image and its corresponding label(s) in a digital storage device (e.g., hard drive, network drive, cloud storage, RAM, etc.).

In step 407, the method may include training a computational pathology-based machine learning algorithm that takes, as input, one or more digital images of a pathology specimen, and predicting a prioritization rank for each digital image. Different methods for implementing the machine learning algorithm may include but are not limited to (1) CNN (Convolutional Neural Network); (2) MIL (Multiple Instance Learning); (3) RNN (Recurrent Neural Network); (4) Feature aggregation via CNN; and/or (5) Feature extraction following by ensemble methods (e.g., random forest), linear/non-linear classifiers (e.g., SVMs, MLP), and/or dimensionality reduction techniques (e.g., PCA, LDA). Example features may include vector embeddings from a CNN, single/multi-class output from a CNN, and/or multi-dimensional output from a CNN (e.g., a mask overlay of the original image). A CNN may learn feature representations for classification tasks directly from pixels, which may lead to better diagnostic performance. When detailed annotations for regions or pixel-wise labels are available, a CNN may be trained directly if there is a large amount of labeled data. However, when labels are only at the whole slide level or over a collection of slides in a group (which may be called a "part" in pathology), MIL may be used to train the CNN or another neural network classifier, where MIL learns the image regions that are diagnostic for the classification task leading to the ability to learn without exhaustive annotations. An RNN may be used on features extracted from multiple image regions (e.g., tiles) that it then processes to make a prediction. Other machine learning methods, e.g., random forest, SVM, and numerous others may be used with either features learned by a CNN, a CNN with MIL, or using hand-crafted image features (e.g., SIFT or SURF) to do the classification task, but they may perform poorly when trained directly from pixels. These methods tend to perform poorly compared to CNN-based systems when there is a large amount of annotated training data available. Dimensionality reduction techniques could be used as a pre-processing step before using any of the classifiers mentioned, which could be useful if there was little data available.

The above description of machine learning algorithms for FIG. 2 (e.g., Table 1 and corresponding description) may also apply to the machine learning algorithms of FIG. 4.

An exemplary method 420 for using the quality control prioritization tool may include one or more of the steps below. In step 421, the method may include receiving a digital pathology image corresponding to a user. In step 423, the method may include determining a rank order or statistic for a slide and/or a case associated with the received digital pathology image. The rank order or statistic may be determined by applying the trained computational pathology-machine learning algorithm (e.g., of method 400) to the received image. The rank order or statistic may be used to prioritize review or additional slide preparation for the slide associated with the received image or the case associated with the received image.

In step 425, the method may include outputting the rank order or statistic. One output may include a determination and/or display of one or more variation(s) in order, based on preferences, heuristics, statistics, objectives of user (e.g., efficiency, difficulty, urgency, etc.). Alternately or in addition, an output may include a visual sorting of the received image at a case level, based on the generated order. For example, such visual sorting may include a display comprising a sorting of cases ordered based on maximum or minimum slide probability for a target feature, based on an average probability across all slides for a target feature, based on the raw number of slides showing a target feature, etc. Another output may include a visualization of a sorting at the slide level or tissue block level within each case, based on the generated order. The visual sorting may be performed by a user, and/or computationally. Yet another output may include an identification of a specific quality control issue and/or an alert to address the identified quality control issue. For example, a quality control metric may be computed for each slide. The quality control metric may signify the presence and/or severity of a quality control issue. The alert may be transmitted to a particular personnel. For example, this step may include identifying personnel associated with an identified quality control issue and generating the alert for the identified personnel. Another aspect of the alert may include a step of discerning if the quality control issue impacts rendering of a diagnosis. In some embodiments, the alert may be generated or prompted only if the identified quality control issue impacts rendering a diagnosis. For example, the alert may be generated only if the quality control metric associated with the quality control issue passes a predetermined quality control metric threshold value.

According to one embodiment, a prioritization may be designed to increase efficiency. Currently, most institutions and laboratories have standardized turnaround time expectations for each pathologist. The time may be measured from the point of accession of a pathology specimen, to sign-out by a primary pathologist. In practice, pathologists may order additional stains or recuts for more information for some cases before rendering a final diagnosis. The additional stain or recut orders may be more numerous in certain pathology subspecialties. The additional orders may increase turnaround time and thus impact the patient. The current embodiment may prioritize these types of subspecialty cases for review, e.g., so that additional stain(s) or recut(s) may be ordered prior to pathologist review, or so that pathologists may review such slide(s) sooner and order the additional stain(s) or recut(s) sooner. Such prioritization may lower turnaround time and raise efficiency of slide review.

Figure 5:
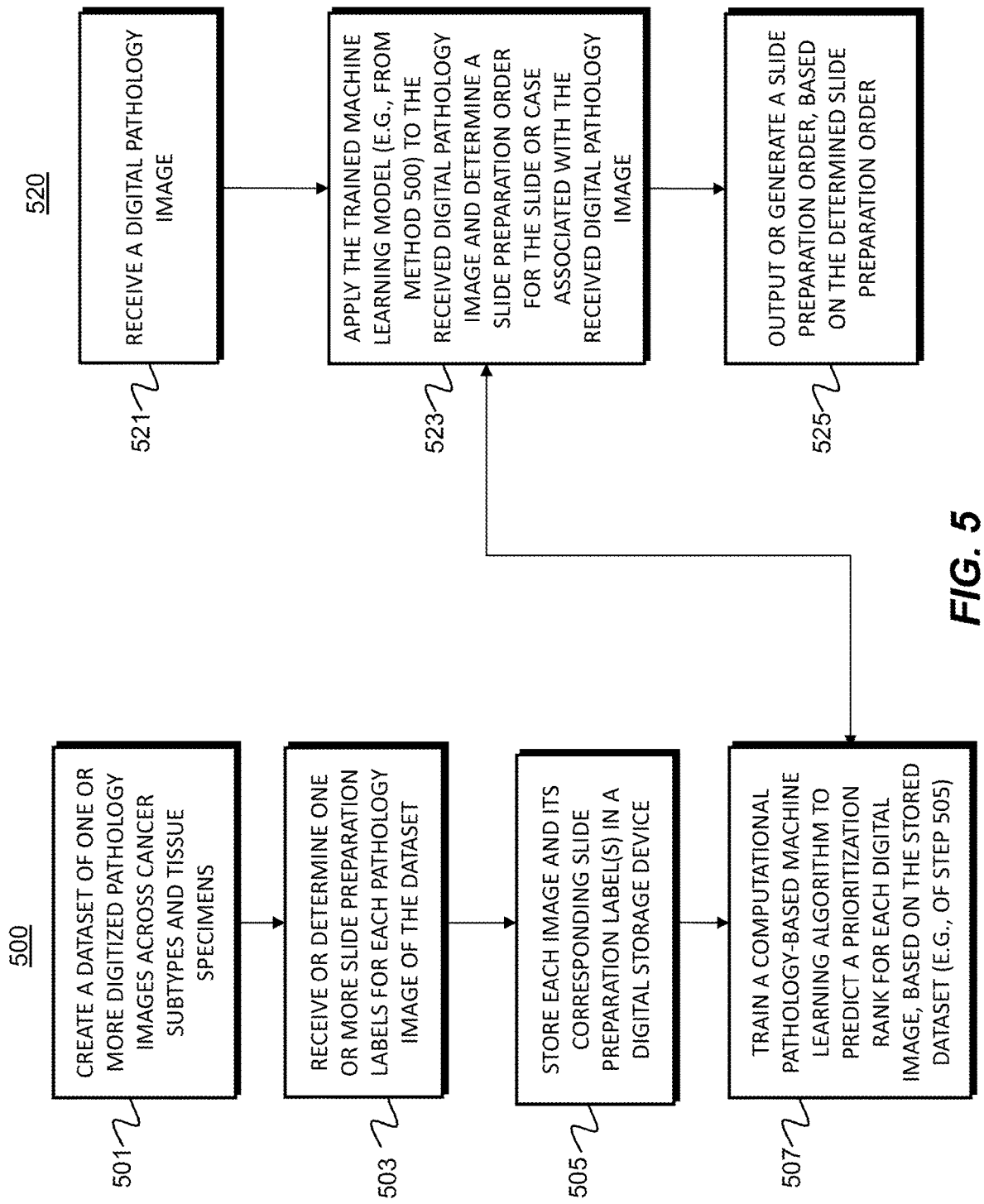
FIG. 5 is a flowchart of an exemplary embodiment of generating and using a pathology slide preparation prioritization tool, with respect to quality control, according to an exemplary embodiment of the present disclosure.

FIG. 5 illustrates exemplary methods for developing an efficiency prioritization tool. For example, exemplary methods 500 and 520 (e.g., steps 501-525) may be performed by the slide prioritization tool 101 automatically or in response to a request from a user (e.g., physician, pathologist, etc.).

According to one embodiment, the exemplary method 500 for developing an efficiency prioritization tool may include one or more of the steps below. In step 501, the method may include creating a dataset of digitized pathology images across cancer subtypes and tissue specimens (e.g., histology, cytology, hematology, microCT, etc.). In step 503, the method may include receiving or determining one or more labels (e.g., slide morphology, diagnostic, outcome, difficulty, etc.) for each pathology image of the dataset. Additional exemplary labels may include but are not limited to the following slide preparation labels: (1) likely need for a specimen recut; (2) likely need for an immunohistochemical stain; (3) Likely need for additional diagnostic testing (e.g., genomic testing); (4) Likely need for a second opinion (consultation); and/or (5) Likely need for a special stain.

In step 505, the method may include storing each image and its corresponding label(s) in a digital storage device (e.g., hard drive, network drive, cloud storage, RAM, etc.). In step 507, the method may include training a computational pathology-based machine learning algorithm that takes, as input, one or more digital images of a pathology specimen, and then predicts a prioritization rank for each digital image. Different methods for implementing the machine learning algorithm may include but are not limited to (1) CNN (Convolutional Neural Network); (2) MIL (Multiple Instance Learning); (3) RNN (Recurrent Neural Network); (4) Feature aggregation via CNN; and/or (5) Feature extraction following by ensemble methods (e.g., random forest), linear/non-linear classifiers (e.g., SVMs, MLP), and/or dimensionality reduction techniques (e.g., PCA, LDA). Example features may include vector embeddings from a CNN, single/multi-class output from a CNN, and/or multi-dimensional output from a CNN (e.g., a mask overlay of the original image). A CNN may learn feature representations for classification tasks directly from pixels, which may lead to better diagnostic performance. When detailed annotations for regions or pixel-wise labels are available, a CNN may be trained directly if there is a large amount of labeled data. However, when labels are only at the whole slide level or over a collection of slides in a group (which may be called a "part" in pathology), MIL may be used to train the CNN or another neural network classifier, where MIL learns the image regions that are diagnostic for the classification task leading to the ability to learn without exhaustive annotations. An RNN may be used on features extracted from multiple image regions (e.g., tiles) that it then processes to make a prediction. Other machine learning methods, e.g., random forest, SVM, and numerous others may be used with either features learned by a CNN, a CNN with MIL, or using hand-crafted image features (e.g., SIFT or SURF) to do the classification task, but they may perform poorly when trained directly from pixels. These methods tend to perform poorly compared to CNN-based systems when there is a large amount of annotated training data available. Dimensionality reduction techniques could be used as a pre-processing step before using any of the classifiers mentioned, which could be useful if there was little data available.

The above description of machine learning algorithms for FIG. 2 (e.g., Table 1 and corresponding description) may also apply to the machine learning algorithms of FIG. 5.

An exemplary method 520 for using the efficiency prioritization tool may include one or more of the steps below. In step 521, the method may include receiving a digital pathology image corresponding to a user. In step 523, the method may include determining a rank order or statistic for a slide and/or a case associated with the received digital pathology image. The rank order or statistic may be determined by applying the trained computational pathology-machine learning algorithm (e.g., of method 500) to the received image. The rank order or statistic may be used to prioritize review or additional slide preparation for the slide associated with the received image or the case associated with the received image.

In step 525, the method may include outputting the rank order or statistic. One output may include a determination and/or display of one or more variation(s) in order, based on preferences, heuristics, statistics, objectives of user (e.g., efficiency, difficulty, urgency, etc.). Alternately or in addition, an output may include a visual sorting of the received image at a case level, based on the generated order. For example, such visual sorting may include a display comprising a sorting of cases ordered based on maximum or minimum slide probability for a target feature, based on an average probability across all slides for a target feature, based on the raw number of slides showing a target feature, etc. The visual sorting may be performed by a user, and/or computationally. Another output may include a visualization of a sorting at the slide level or block level within each case, based on the generated order. Yet another output may include a stain or recut location recommendation. Yet another output may include generating an order or "pre-order" of predicted stain order(s), recut order(s), test(s) or consultation(s).

According to one embodiment, slide prioritization may be based on diagnostic features. Pathologists may have varying years and types of experience, and levels of access to resources. General pathologists, for example, may review a broad range of specimen types with diverse diagnoses. With the increase in case volume and decrease in new pathologists, practicing pathologists may be under pressure to review diverse and large volumes of cases. The following embodiment may include feature identification to aid pathologists in triaging cases/slides. The feature identification may include visual aids for image features in digitized pathology slide/case images, where the image features that could have otherwise been missed or overlooked.

Figure 6:
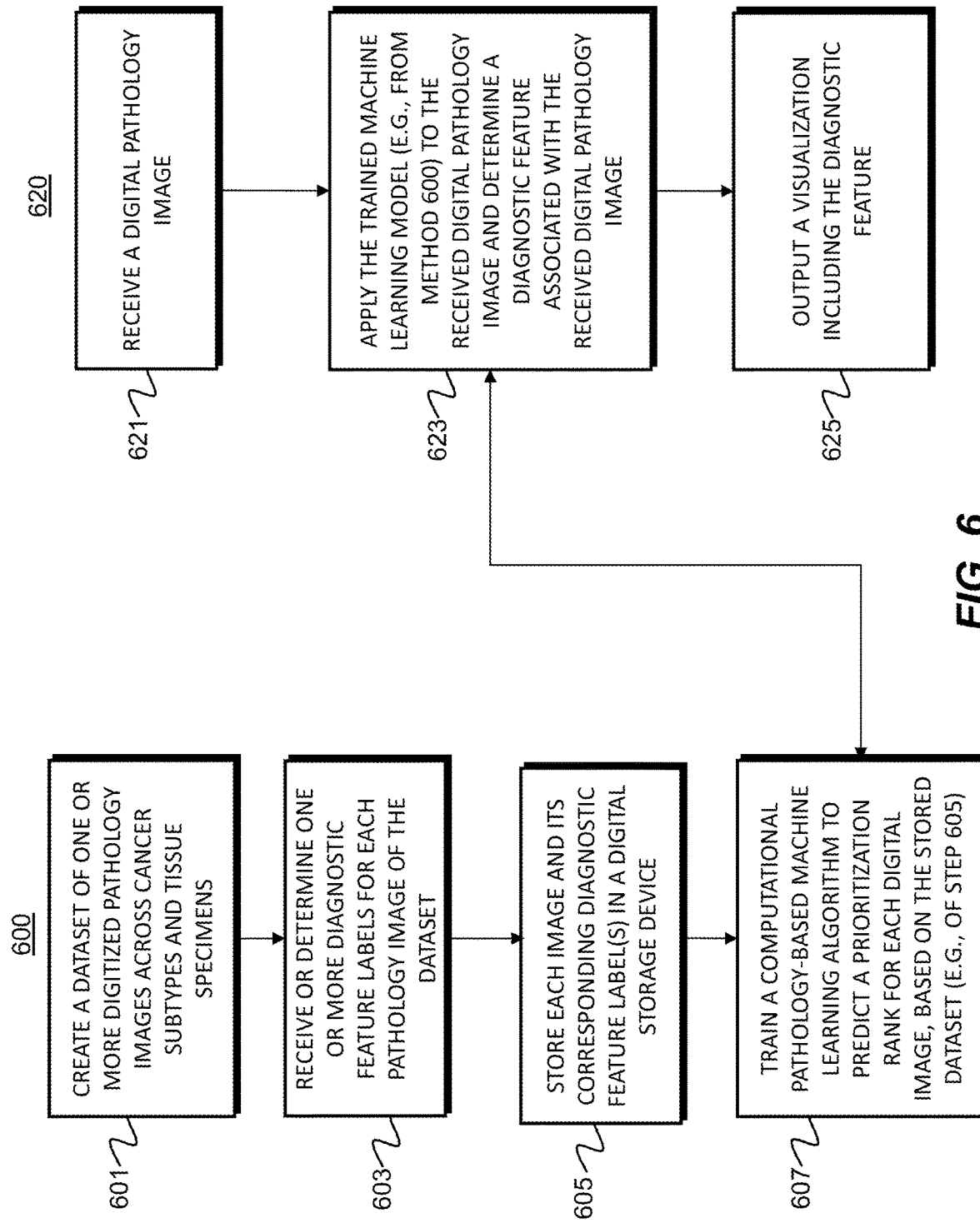
FIG. 6 is a flowchart of an exemplary embodiment of generating and using a diagnostic feature prioritization tool, according to an exemplary embodiment of the present disclosure.

FIG. 6 illustrates exemplary methods for developing a diagnostic feature prioritization tool. For example, exemplary methods 600 and 620 (e.g., steps 601-625) may be performed by the slide prioritization tool 101 automatically or in response to a request from a user (e.g., physician, pathologist, etc.).

According to one embodiment, the exemplary method 600 for developing a diagnostic feature prioritization tool may include one or more of the steps below. In step 601, the method may include creating a dataset of digitized pathology images across cancer subtypes and tissue specimens (e.g., histology, cytology, hematology, microCT, etc.). In step 603, the method may include one or more labels (e.g., slide morphology, diagnostic, outcome, difficulty, etc.) for each pathology image of the dataset. Additional exemplary diagnostic feature labels may include but are not limited to cancer presence, cancer grade, cancer close to a surgical margin, treatment effects, precancerous lesions, and features suggestive of presence of infectious organisms (e.g., viral, fungal, bacterial, parasite, etc.). In step 605, the method may include storing each image and its corresponding label(s) in a digital storage device (e.g., hard drive, network drive, cloud storage, RAM, etc.).

In step 607, the method may include training a computational pathology-based machine learning algorithm that takes, as input, one or more digital images of a pathology specimen, and then predicts a prioritization rank for each digital image. Different methods for implementing the machine learning algorithm may include but are not limited to (1) CNN (Convolutional Neural Network); (2) MIL (Multiple Instance Learning); (3) RNN (Recurrent Neural Network); (4) Feature aggregation via CNN; and/or (5) Feature extraction following by ensemble methods (e.g., random forest), linear/non-linear classifiers (e.g., SVMs, MLP), and/or dimensionality reduction techniques (e.g., PCA, LDA). Example features may include vector embeddings from a CNN, single/multi-class output from a CNN, and/or multi-dimensional output from a CNN (e.g., a mask overlay of the original image). A CNN may learn feature representations for classification tasks directly from pixels, which may lead to better diagnostic performance. When detailed annotations for regions or pixel-wise labels are available, a CNN may be trained directly if there is a large amount of labeled data. However, when labels are only at the whole slide level or over a collection of slides in a group (which may be called a "part" in pathology), MIL may be used to train the CNN or another neural network classifier, where MIL learns the image regions that are diagnostic for the classification task leading to the ability to learn without exhaustive annotations. An RNN may be used on features extracted from multiple image regions (e.g., tiles) that it then processes to make a prediction. Other machine learning methods, e.g., random forest, SVM, and numerous others may be used with either features learned by a CNN, a CNN with MIL, or using hand-crafted image features (e.g., SIFT or SURF) to do the classification task, but they may perform poorly when trained directly from pixels. These methods tend to perform poorly compared to CNN-based systems when there is a large amount of annotated training data available. Dimensionality reduction techniques could be used as a pre-processing step before using any of the classifiers mentioned, which could be useful if there was little data available.

The above description of machine learning algorithms for FIG. 2 (e.g., Table 1 and corresponding description) may also apply to the machine learning algorithms of FIG. 6.

An exemplary method 620 for using the diagnostic feature prioritization tool may include one or more of the steps below. In step 621, the method may include receiving a digital pathology image corresponding to a user. In step 623, the method may include determining a rank order or statistic for a slide and/or a case associated with the received digital pathology image. The rank order or statistic may be determined by applying the trained computational pathology-machine learning algorithm (e.g., of method 600) to the received image. The rank order or statistic may be used to prioritize review or additional slide preparation for the slide associated with the received image or the case associated with the received image. The rank order or statistic in this case may include statistic(s) associated with diagnostic features detected in the digital pathology image.

In step 625, the method may include outputting the rank order or statistic. One output may include a determination and/or display of one or more variation(s) in order, based on preferences, heuristics, statistics, objectives of user (e.g., efficiency, difficulty, urgency, etc.). Alternately or in addition, an output may include a visual sorting of the received image at a case level, based on the generated order. For example, such visual sorting may include a display comprising a sorting of cases ordered based on maximum or minimum slide probability for a target feature, based on an average probability across all slides for a target feature, based on the raw number of slides showing a target feature, etc. The visual sorting may be performed by a user, and/or computationally. Another output may include a visualization of a sorting at the slide level or block level within each case, based on the generated order. Yet another output may include a list, visual indication, or alert for one or more identified diagnostic features. One embodiment may include an option or menu interface for a user to select one (or any combination) of diagnostic features for prioritization of review.

According to one embodiment, a slide prioritization may be based on urgency. A diagnosis may be critical to a patient's medical process. Prioritizing pathology review/diagnosis based on a case's clinical urgency may streamline the communication between surgeon, pathologist, clinician, and patient. Urgency may be difficult to detect, since many clinical scenarios involve a patient with no prior history of cancer, who presents with a "mass" in their body. The result may be a first time, unexpected cancer diagnosis. In such cases where no knowledge is nonexistent or unavailable, "user input" may define when a case is considered "urgent." For example, a clinician may call a pathologist and indicate that a given case is urgent. In such situations, a person/clinician may have requested that the case be rushed. Currently, a clinician may manually label a specimen as having, "RUSH" status. The specimen may comprise a "mass" from a patient with a newly suspected cancer diagnosis. The RUSH status may be communicated to a pathologist handling the specimen/case. When the pathologist receives a set of completed slides, the pathologist may prioritize reviewing the slides associated with "RUSH" specimens.

Figure 7:
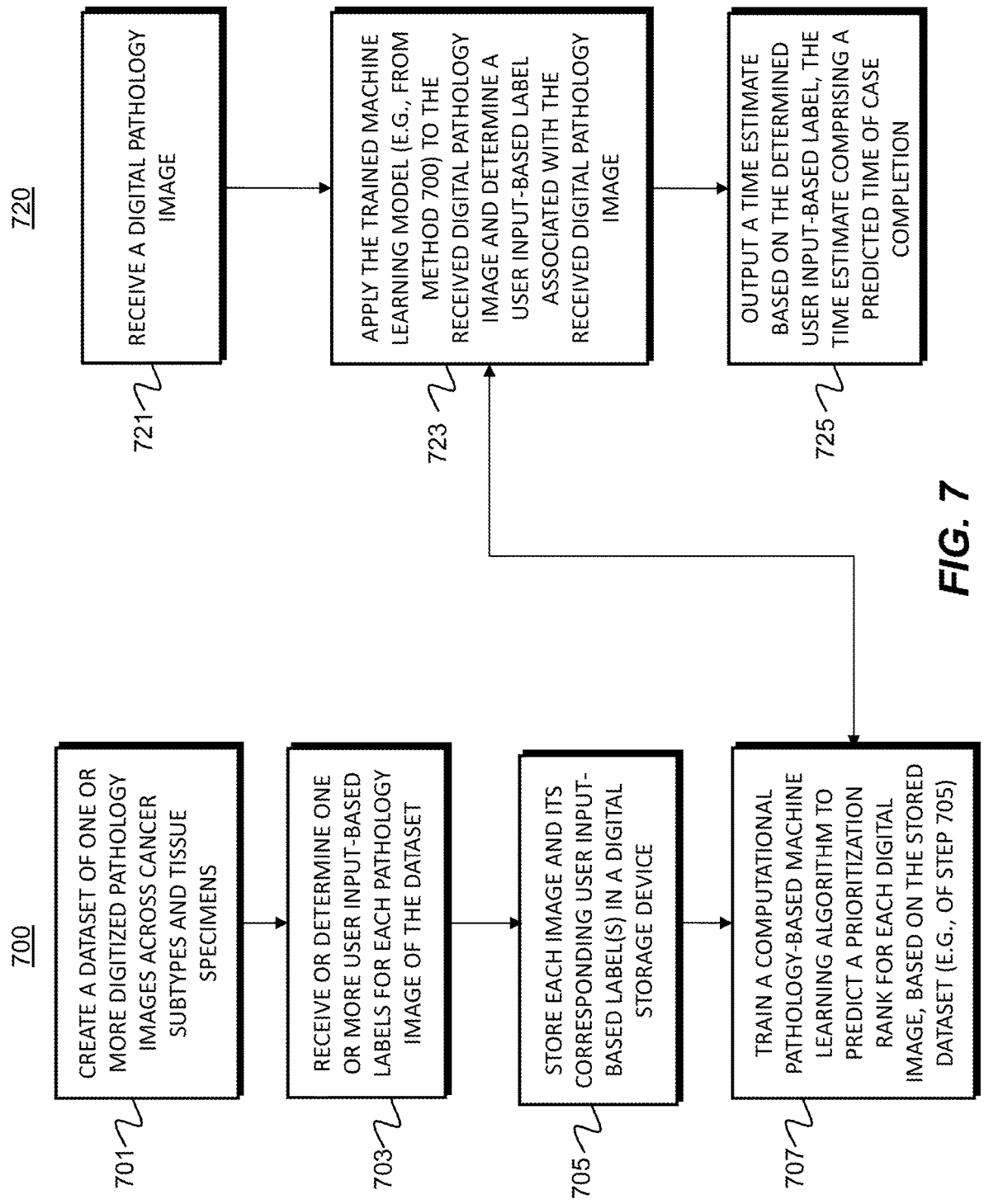
FIG. 7 is a flowchart of an exemplary embodiment of generating and using a pathology slide processing prioritization tool, according to an exemplary embodiment of the present disclosure.

FIG. 7 illustrates exemplary methods for developing a user input-based prioritization tool. For example, exemplary methods 700 and 720 (e.g., steps 701-725) may be performed by the slide prioritization tool 101 automatically or in response to a request from a user (e.g., physician, pathologist, etc.).

According to one embodiment, the exemplary method 700 for developing a user input-based prioritization tool may include one or more of the steps below. In step 701, the method may include creating a dataset of digitized pathology images across cancer subtypes and tissue specimens (e.g., histology, cytology, hematology, microCT, etc.). In step 703, the method may include receiving or determining one or more labels (e.g., slide morphology, diagnostic, outcome, difficulty, etc.) for each pathology image of the dataset. Additional exemplary user-based priority labels may include patient urgency, diagnostic relevance to clinical question, clinical trial enrollment, presented risk factors, and/or user input. In step 705, the method may include storing each image and its corresponding label(s) in a digital storage device (e.g., hard drive, network drive, cloud storage, RAM, etc.).

In step 707, the method may include training a computational pathology-based machine learning algorithm that takes, as input, one or more digital images of a pathology specimen, and then predicts a prioritization rank for each digital image. Different method for implementing the machine learning algorithm may include, but are not limited to (1) CNN (Convolutional Neural Network); (2) MIL (Multiple Instance Learning); (3) RNN (Recurrent Neural Network); (4) Feature aggregation via CNN; and/or (5) Feature extraction following by ensemble methods (e.g., random forest), linear/non-linear classifiers (e.g., SVMs, MLP), and/or dimensionality reduction techniques (e.g., PCA, LDA). Example features may include vector embeddings from a CNN, single/multi-class output from a CNN, and/or multi-dimensional output from a CNN (e.g., a mask overlay of the original image). A CNN may learn feature representations for classification tasks directly from pixels, which may lead to better diagnostic performance. When detailed annotations for regions or pixel-wise labels are available, a CNN may be trained directly if there is a large amount of labeled data. However, when labels are only at the whole slide level or over a collection of slides in a group (which may be called a "part" in pathology), MIL may be used to train the CNN or another neural network classifier, where MIL learns the image regions that are diagnostic for the classification task leading to the ability to learn without exhaustive annotations. An RNN may be used on features extracted from multiple image regions (e.g., tiles) that it then processes to make a prediction. Other machine learning methods, e.g., random forest, SVM, and numerous others may be used with either features learned by a CNN, a CNN with MIL, or using hand-crafted image features (e.g., SIFT or SURF) to do the classification task, but they may perform poorly when trained directly from pixels. These methods tend to perform poorly compared to CNN-based systems when there is a large amount of annotated training data available. Dimensionality reduction techniques could be used as a pre-processing step before using any of the classifiers mentioned, which could be useful if there was little data available.

The above description of machine learning algorithms for FIG. 2 (e.g., Table 1 and corresponding description) may also apply to the machine learning algorithms of FIG. 7.

An exemplary method 720 for using the user input-based prioritization tool may include one or more of the steps below. In step 721, the method may include receiving a digital pathology image corresponding to a user. In step 723, the method may include determining a rank order or statistic for a slide and/or a case associated with the received digital pathology image. The rank order or statistic may be determined by applying the trained computational pathology-machine learning algorithm (e.g., of method 700) to the received image. The rank order or statistic may be used to prioritize review or additional slide preparation for the slide associated with the received image or the case associated with the received image. The rank order or statistic in this case may include statistic(s) associated with diagnostic features detected in the digital pathology image.

In step 725, the method may include outputting the rank order or statistic. One output may include a determination and/or display of one or more variation(s) in order, based on preferences, heuristics, statistics, objectives of a user (e.g., efficiency, difficulty, urgency, etc.). Alternately or in addition, an output may include a visual sorting of the received image at a case level, based on the generated order. For example, such visual sorting may include a display comprising a sorting of cases ordered based on maximum or minimum slide probability for a target feature, based on an average probability across all slides for a target feature, based on the raw number of slides showing a target feature, etc. The visual sorting may be performed by a user, and/or computationally. Another output may include a visualization of a sorting at the slide level or block level within each case, based on the generated order. Yet another output may include a time estimate for case completion, based on the determined rank order or statistic (e.g., step 725). The time estimate may be based on the algorithm of method 700, as well as other slides/cases in queue for slide preparation or processing. The output may include providing the time estimate to a physician. A further embodiment may include notifying a referring physician when a report, diagnosis, or slide preparation is completed.

Figure 8:
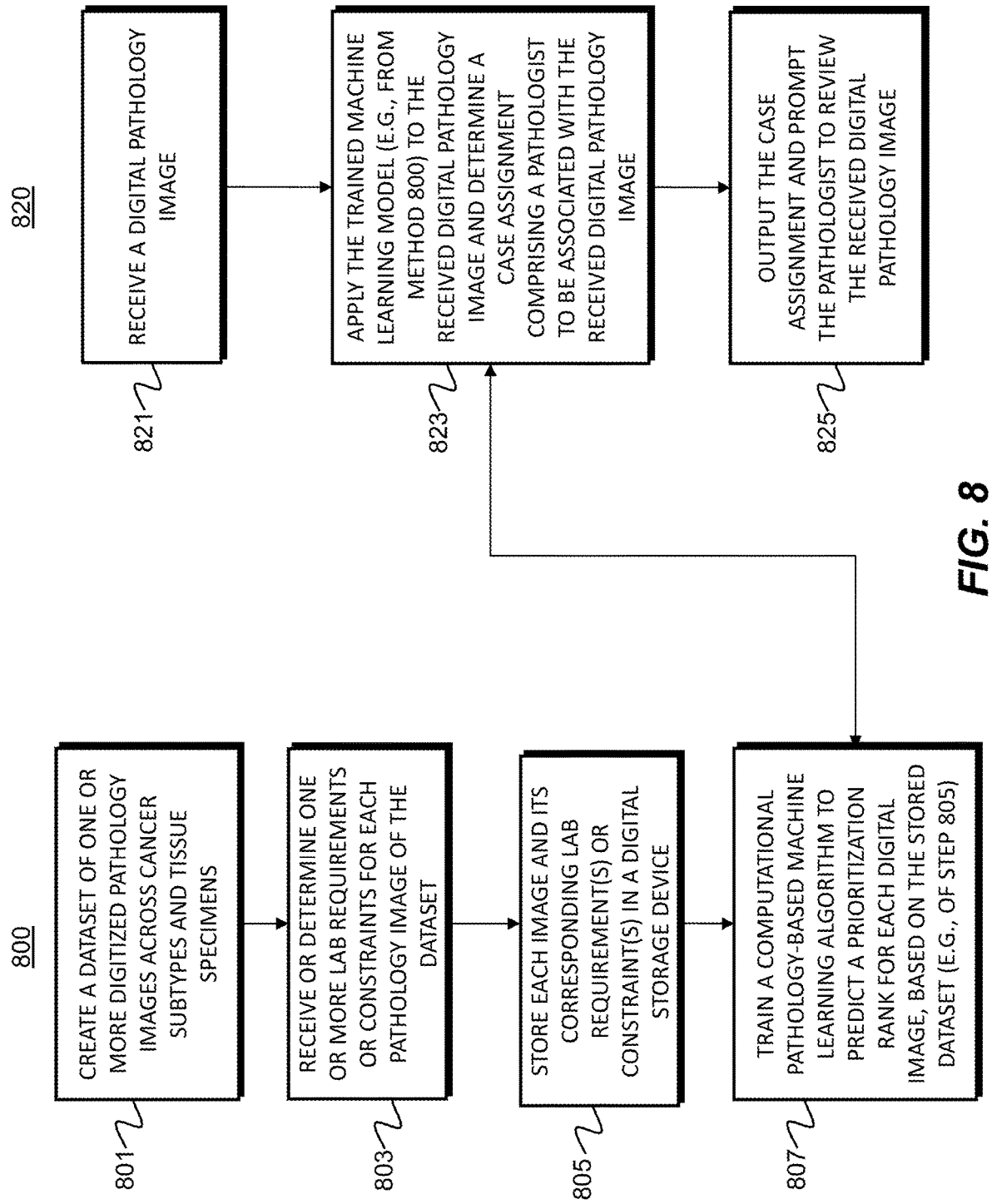
FIG. 8 is a flowchart of an exemplary embodiment of generating and using a pathology slide review and assignment prioritization tool, according to an exemplary embodiment of the present disclosure.

FIG. 8 illustrates exemplary methods for prioritizing and distributing cases to pathologists to meet an institution's required turnaround time (e.g., 48 hours) per case, patient urgency needs, staffing constraints, etc., according to an exemplary embodiment of the present disclosure. For example, exemplary methods 800 and 820 (e.g., steps 801-825) may be performed by the slide prioritization tool 101 automatically in response to a request from a user (e.g., physician, pathologist, etc.).

According to one embodiment, a method may include prioritizing and distributing cases to pathologists to meet an institution's required turnaround time (e.g., 48 hours) per case, patient urgency needs, staffing constraints, etc. As illustrated in FIG. 8, an exemplary method 800 for developing a case assignment prioritization tool may include one or more of the steps below. In step 801, the method may include creating a dataset of digitized pathology images across cancer subtypes and tissue specimens (e.g., histology, cytology, hematology, microCT, etc.). In step 803, the method may include receiving or determining one or more labels (e.g., slide morphology, diagnostic, outcome, difficulty, etc.) for each pathology image of the dataset. Step 803 may include receiving additional input(s), e.g., institution/lab network/histology lab/pathologist requirements and/or constraints. In step 805, the method may include storing each image and its corresponding label(s) in a digital storage device (e.g., hard drive, network drive, cloud storage, RAM, etc.).

In step 807, the method may include training a computational pathology-based machine learning algorithm that takes, as input, (1) one or more digital images of a pathology specimen and/or (2) system/workflow requirements/constraints, and then predicts a prioritization rank for each digital image (e.g., step 807). Different methods for implementing the machine learning algorithm may include but are not limited to (1) CNN (Convolutional Neural Network); (2) MIL (Multiple Instance Learning); (3) RNN (Recurrent Neural Network); (4) Feature aggregation via CNN; and/or (5) Feature extraction following by ensemble methods (e.g., random forest), linear/non-linear classifiers (e.g., SVMs, MLP), and/or dimensionality reduction techniques (e.g., PCA, LDA). Example features may include vector embeddings from a CNN, single/multi-class output from a CNN, and/or multi-dimensional output from a CNN (e.g., a mask overlay of the original image). A CNN may learn feature representations for classification tasks directly from pixels, which may lead to better diagnostic performance. When detailed annotations for regions or pixel-wise labels are available, a CNN may be trained directly if there is a large amount of labeled data. However, when labels are only at the whole slide level or over a collection of slides in a group (which may be called a "part" in pathology), MIL may be used to train the CNN or another neural network classifier, where MIL learns the image regions that are diagnostic for the classification task leading to the ability to learn without exhaustive annotations. An RNN may be used on features extracted from multiple image regions (e.g., tiles) that it then processes to make a prediction. Other machine learning methods, e.g., random forest, SVM, and numerous others may be used with either features learned by a CNN, a CNN with MIL, or using hand-crafted image features (e.g., SIFT or SURF) to do the classification task, but they may perform poorly when trained directly from pixels. These methods tend to perform poorly compared to CNN-based systems when there is a large amount of annotated training data available. Dimensionality reduction techniques could be used as a pre-processing step before using any of the classifiers mentioned, which could be useful if there was little data available.

The above description of machine learning algorithms for FIG. 2 (e.g., Table 1 and corresponding description) may also apply to the machine learning algorithms of FIG. 8.

An exemplary method 820 for using the case assignment prioritization tool may include one or more of the steps below. In step 821, the method may include receiving a digital pathology image corresponding to a user. In step 823, the method may include determining a rank order or statistic for a slide and/or a case associated with the received digital pathology image. The rank order or statistic may be determined by applying the trained computational pathology-machine learning algorithm (e.g., of method 800) to the received image. The rank order or statistic may be used to prioritize review or additional slide preparation for the slide associated with the received image or the case associated with the received image. The rank order or statistic in this case may include statistic(s) associated with diagnostic features detected in the digital pathology image.

In step 825, the method may include outputting the rank order or statistic. One output may include a determination and/or display of one or more variation(s) in order, based on preferences, heuristics, statistics, objectives of user (e.g., efficiency, difficulty, urgency, etc.). Alternately or in addition, an output may include a visual sorting of the received image at a case level, based on the generated order. For example, such visual sorting may include a display comprising a sorting of cases ordered based on maximum or minimum slide probability for a target feature, based on an average probability across all slides for a target feature, based on the raw number of slides showing a target feature, etc. The visual sorting may be performed by a user, and/or computationally. Another output may include a visualization of a sorting at the slide level or block level within each case, based on the generated order. Yet another output may include generating a distribution and/or assignment of cases within a pathology or subspecialty medical team, or within a network of pathologist(s). A further embodiment may include assigning cases to specific pathologists, or a set of pathologists. The generated distribution or assignment may be optimized, based on medical practitioner availability, prior experience level, medical specialty, patient roster, and/or institution/lab requirements and constraints.

Figure 9:
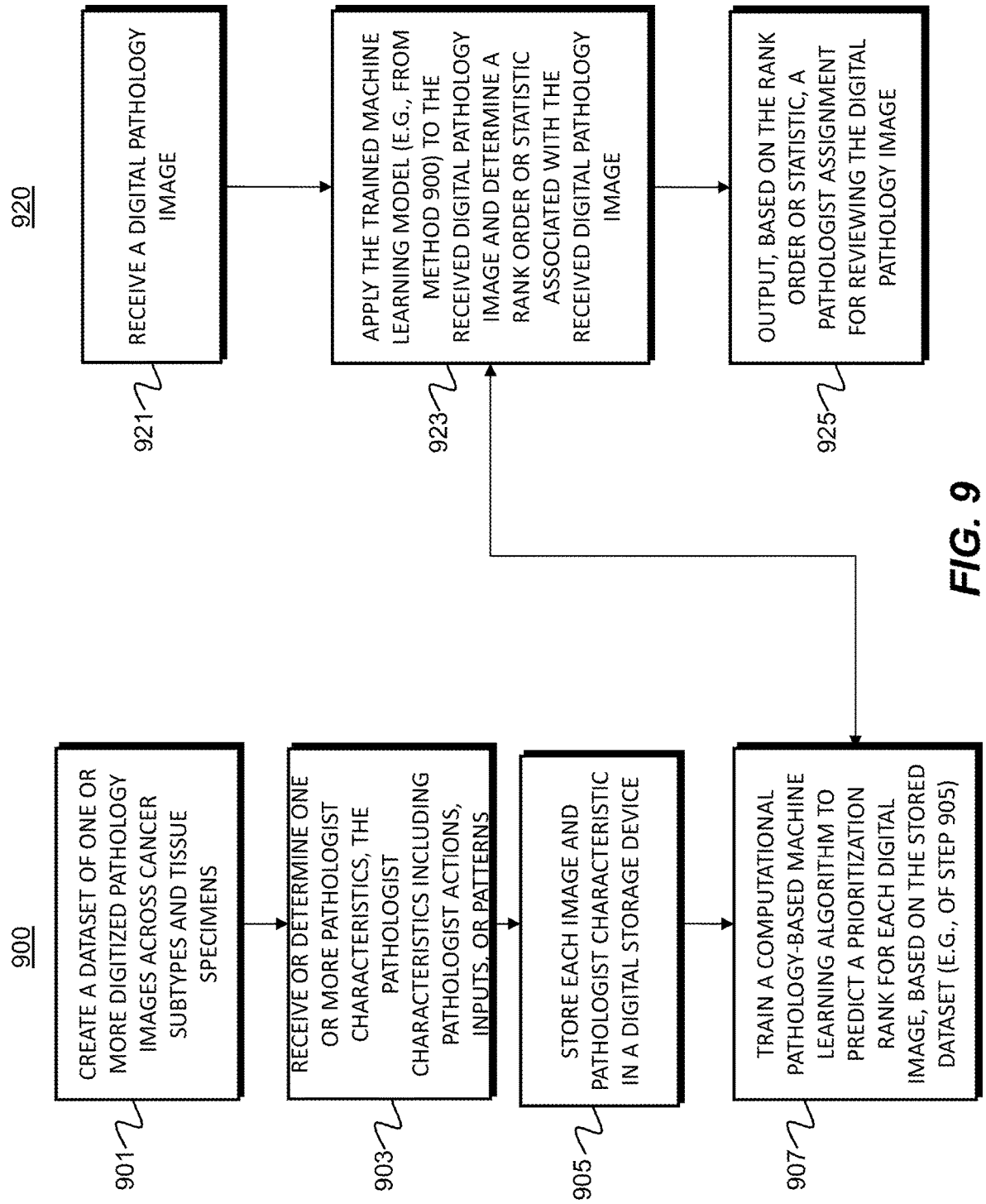
FIG. 9 is a flowchart of an exemplary embodiment of generating and using a personalized pathology slide prioritization tool, according to an exemplary embodiment of the present disclosure.

FIG. 9 illustrates exemplary methods for continually learning and optimizing a prioritization system, based on patterns it learns from a pathologist, according to an exemplary embodiment of the present disclosure. For example, exemplary methods 900 and 920 (e.g., steps 901-925) may be performed by the slide prioritization tool 101 automatically or in response to a request from a user (e.g., physician, pathologist, etc.). This learning and optimization process may take place while the tool is in use. Such a continual learning and optimization may allow pathologists to experience a prioritization tool tailored to their preferences (e.g., viewing difficult cases before easy cases) and habits (e.g., place order for certain stains for specific specimens).

According to one embodiment, the exemplary method 900 for developing a personalized tool including one or more of the steps below. In step 901, the method may include creating a dataset of digitized pathology images across cancer subtypes and tissue specimens (e.g., histology, cytology, hematology, microCT, etc.). In step 903, the method may include receiving or determining one or more labels (e.g., slide morphology, diagnostic, outcome, difficulty, etc.) for each pathology image of the dataset. Step 903 may include receiving or detecting additional input(s), e.g., user actions, inputs (e.g., preferences), or patterns. In step 905, the method may include storing each image and its corresponding label(s) in a digital storage device (e.g., hard drive, network drive, cloud storage, RAM, etc.).

In step 907, the method may include training a computational pathology-based machine learning algorithm that takes, as input, (1) one or more digital images of a pathology specimen and/or (2) user actions, inputs, or patterns, and then predicts a prioritization rank for each digital image (e.g., step 907). Different methods for implementing the machine learning algorithm may include but are not limited to (1) CNN (Convolutional Neural Network); (2) MIL (Multiple Instance Learning); (3) RNN (Recurrent Neural Network); (4) Feature aggregation via CNN; and/or (5) Feature extraction following by ensemble methods (e.g., random forest), linear/non-linear classifiers (e.g., SVMs, MLP), and/or dimensionality reduction techniques (e.g., PCA, LDA). Example features may include vector embeddings from a CNN, single/multi-class output from a CNN, and/or multi-dimensional output from a CNN (e.g., a mask overlay of the original image). A CNN may learn feature representations for classification tasks directly from pixels, which may lead to better diagnostic performance. When detailed annotations for regions or pixel-wise labels are available, a CNN may be trained directly if there is a large amount of labeled data. However, when labels are only at the whole slide level or over a collection of slides in a group (which may be called a "part" in pathology), MIL may be used to train the CNN or another neural network classifier, where MIL learns the image regions that are diagnostic for the classification task leading to the ability to learn without exhaustive annotations. An RNN may be used on features extracted from multiple image regions (e.g., tiles) that it then processes to make a prediction. Other machine learning methods, e.g., random forest, SVM, and numerous others may be used with either features learned by a CNN, a CNN with MIL, or using hand-crafted image features (e.g., SIFT or SURF) to do the classification task, but they may perform poorly when trained directly from pixels. These methods tend to perform poorly compared to CNN-based systems when there is a large amount of annotated training data available. Dimensionality reduction techniques could be used as a pre-processing step before using any of the classifiers mentioned, which could be useful if there was little data available.

The above description of machine learning algorithms for FIG. 2 (e.g., Table 1 and corresponding description) may also apply to the machine learning algorithms of FIG. 9.

An exemplary method 920 for using the tool may include one or more of the steps below. In step 921, the method may include receiving a digital pathology image corresponding to a user. In step 923, the method may include determining a rank order or statistic for a slide and/or a case associated with the received digital pathology image. The rank order or statistic may be determined by applying the trained computational pathology-machine learning algorithm (e.g., of method 900) to the received image. The rank order or statistic may be used to prioritize review or additional slide preparation for the slide associated with the received image or the case associated with the received image. The rank order or statistic in this case may include statistic(s) associated with diagnostic features detected in the digital pathology image.

In step 925, the method may include outputting the rank order or statistic. One output may include a determination and/or display of one or more variation(s) in order, based on preferences, heuristics, statistics, objectives of user (e.g., efficiency, difficulty, urgency, etc.). Alternately or in addition, an output may include a visual sorting of the received image at a case level, based on the generated order. For example, such visual sorting may include a display comprising a sorting of cases ordered based on maximum or minimum slide probability for a target feature, based on an average probability across all slides for a target feature, based on the raw number of slides showing a target feature, etc. The visual sorting may be performed by a user, and/or computationally. Another output may include a visualization of a sorting at the slide level or block level within each case, based on the generated order. Yet another output may include generating a distribution and/or assignment of cases within a pathology or subspecialty medical team, or within a network of pathologist(s), e.g., based on individual pathologist preferences, strengths, weaknesses, availability, etc.

According to one embodiment, a method may include optimizing for educating and evaluating pathologists, medical students, pathology residents, researchers, etc. To become a skilled pathologist, medical students and pathology residents may see many slides or slide images to become adept at this skill. This embodiment aims to make this learning process more efficient by presenting digital pathology images to a user that provide the most educational benefit. For example, the presented pathology image may display a prototype of a certain disease, or a common point of confusion/error in detecting a disease. This embodiment may be directed at predicting and selecting an image that practitioners may have the most to learn from, or by using spaced repetition mechanisms. Predicted educational value for an image may be computed based on a function of how difficult the image is to classify, whether a user has previously erred in identifying image properties of the image or in their diagnosis based on the image, whether the user should refresh their knowledge on that image, using a machine learning model (e.g., active learning or a model of the user), etc.

Figure 10:
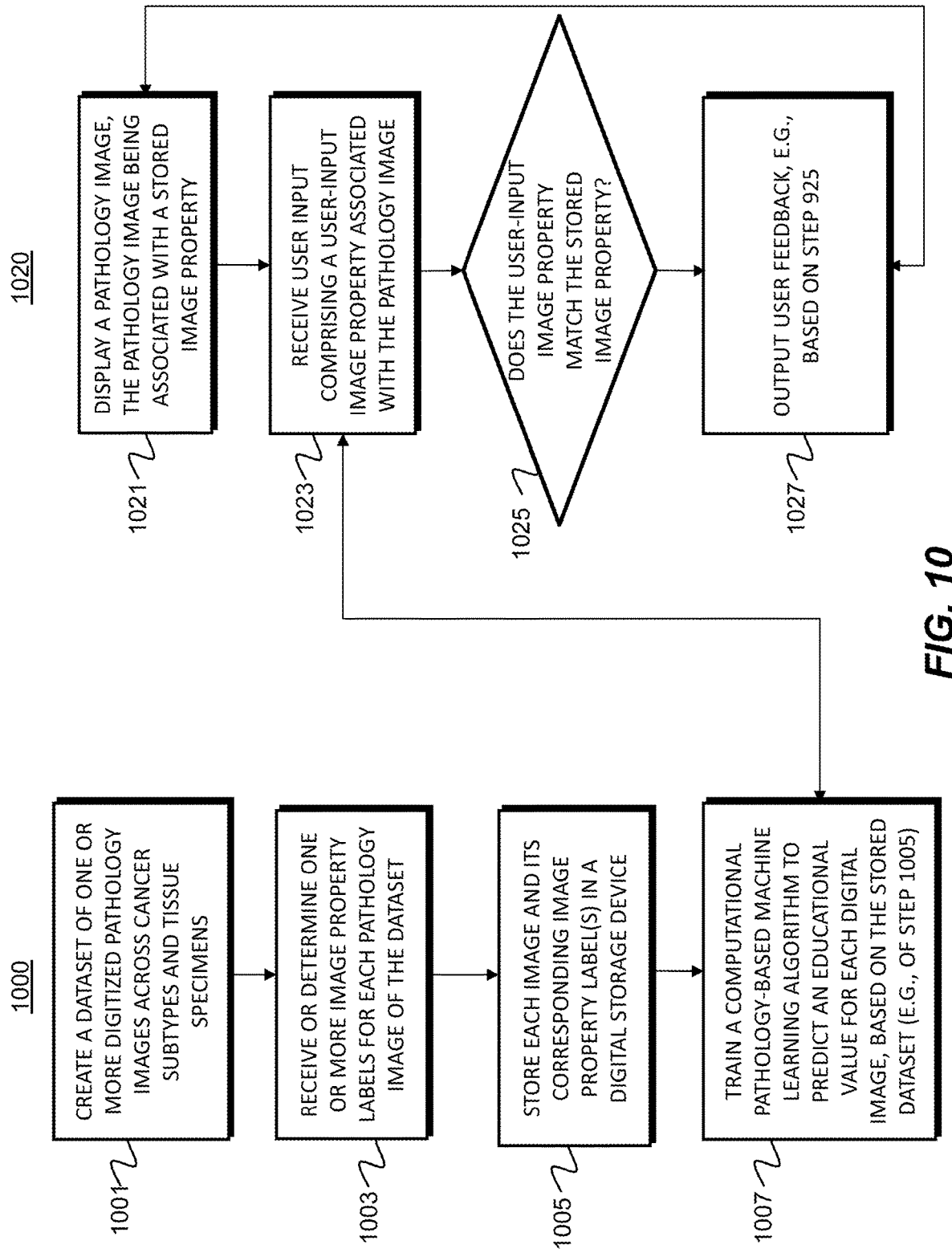
FIG. 10 is a flowchart of an exemplary embodiment of generating and using an educational pathology slide prioritization tool, according to an exemplary embodiment of the present disclosure.

FIG. 10 illustrates exemplary methods for generating and using an educational pathology slide prioritization tool, according to an exemplary embodiment of the present disclosure. For example, exemplary methods 1000 and 1020 (e.g., steps 1001-1027) may be performed by the slide prioritization tool 101 automatically or in response to a request from a user (e.g., physician, pathologist, etc.).

According to one embodiment, the exemplary method 1000 for developing an educational tool may include one or more of the steps below. In step 1001, the method may include creating a dataset of digitized pathology images across cancer subtypes and tissue specimens (e.g., histology, cytology, hematology, microCT, etc.). In step 1003, the method may include receiving or determining one or more image property labels (e.g., slide morphology, diagnostic, outcome, difficulty, etc.) for each pathology image of the dataset. In step 1005, the method may include storing each image and its corresponding label(s) in a digital storage device (e.g., hard drive, network drive, cloud storage, RAM, etc.). In step 1007, the method may include training a computational pathology-based machine learning algorithm that takes, as input, one or more digital images of a pathology specimen, and then predicts an educational value for each digital image. Different methods for implementing the machine learning algorithm may include but are not limited to (1) CNN (Convolutional Neural Network); (2) MIL (Multiple Instance Learning); (3) RNN (Recurrent Neural Network); (4) Feature aggregation via CNN; and/or (5) Feature extraction following by ensemble methods (e.g., random forest), linear/non-linear classifiers (e.g., SVMs, MLP), and/or dimensionality reduction techniques (e.g., PCA, LDA). Example features may include vector embeddings from a CNN, single/multi-class output from a CNN, and/or multi-dimensional output from a CNN (e.g., a mask overlay of the original image). A CNN may learn feature representations for classification tasks directly from pixels, which may lead to better diagnostic performance. When detailed annotations for regions or pixel-wise labels are available, a CNN may be trained directly if there is a large amount of labeled data. However, when labels are only at the whole slide level or over a collection of slides in a group (which may be called a "part" in pathology), MIL may be used to train the CNN or another neural network classifier, where MIL learns the image regions that are diagnostic for the classification task leading to the ability to learn without exhaustive annotations. An RNN may be used on features extracted from multiple image regions (e.g., tiles) that it then processes to make a prediction. Other machine learning methods, e.g., random forest, SVM, and numerous others may be used with either features learned by a CNN, a CNN with MIL, or using hand-crafted image features (e.g., SIFT or SURF) to do the classification task, but they may perform poorly when trained directly from pixels. These methods tend to perform poorly compared to CNN-based systems when there is a large amount of annotated training data available. Dimensionality reduction techniques could be used as a pre-processing step before using any of the classifiers mentioned, which could be useful if there was little data available.

The above description of machine learning algorithms for FIG. 2 (e.g., Table 1 and corresponding description) may also apply to the machine learning algorithms of FIG. 10.

An exemplary method 1020 for using the educational tool may include one or more of the steps below. In step 1021, the method may include displaying, to a user (e.g., a pathology trainee), a pathology image predicted to have an educational value. In step 1023, the method may include receiving a user input denoting one or more properties of the image. The user input may include an estimate of an image property, e.g., a cancer grade. In step 1025, the method may include storing the user's input and/or revising an image difficulty metric associated with the displayed image. The tool may further store a score of the user's input relative to stored image properties.

In step 1027, the tool may provide feedback to a user, regarding whether the user input was correct. The feedback may further include indicators to aid the user in improving their identification of image properties. Exemplary indicators of stored image properties may denote where a user should have looked to identify key image properties, e.g., by highlighting a region with cancer. These indicators may help a user learn where they should have looked. The feedback may further identify diagnostic areas that a user may improve upon, for example, where a user consistently fails to identify key image properties. This tool usage may be iterative. For example, a tool may train a user by displaying another image, either based on a user's ability (or inability) to identify stored image properties, based on user command, or a combination thereof.

Figure 11:
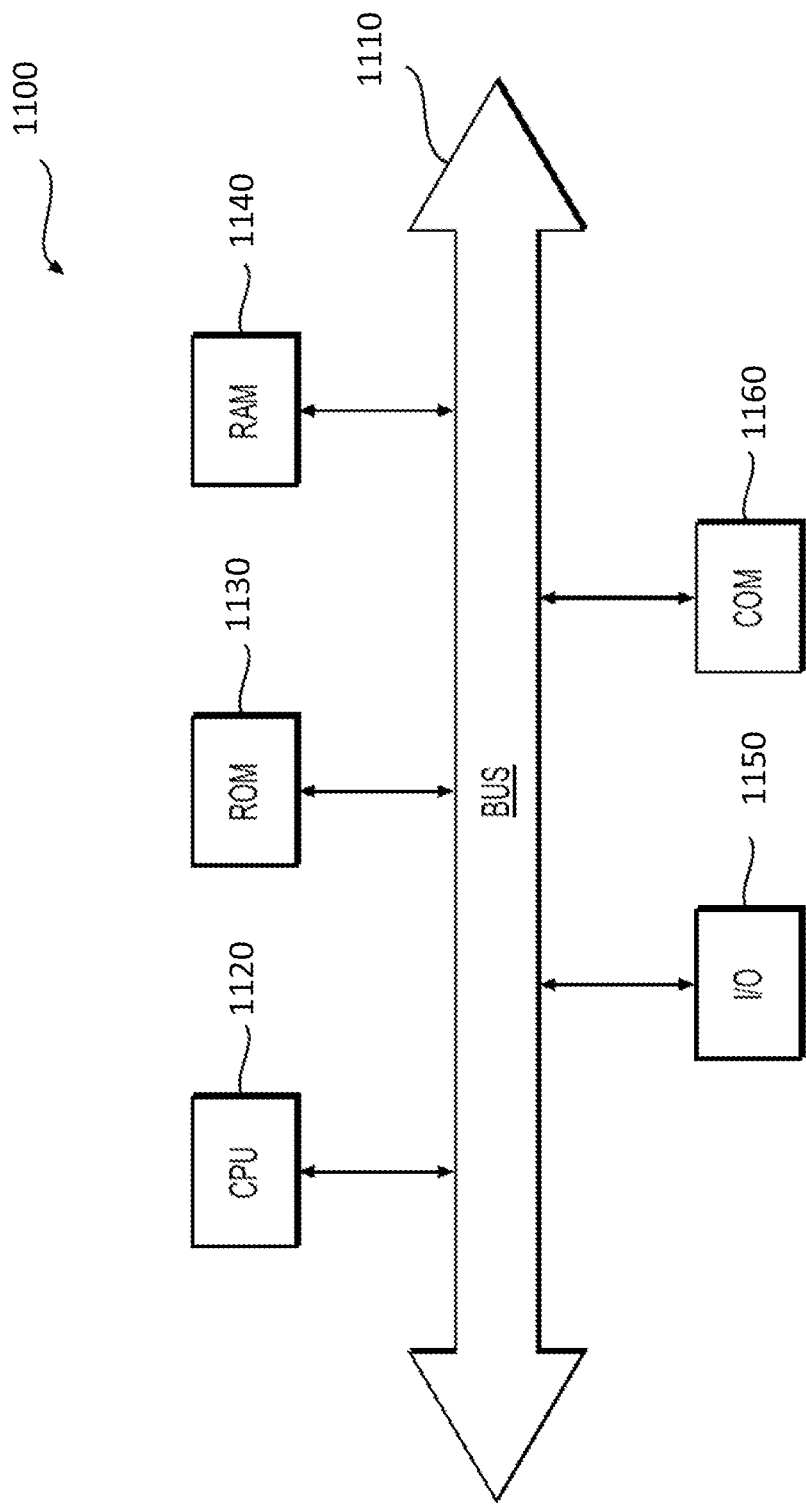
FIG. 11 depicts an example system that may execute techniques presented herein.

As shown in FIG. 11, device 1100 may include a central processing unit (CPU) 1120. CPU 1120 may be any type of processor device including, for example, any type of special purpose or a general-purpose microprocessor device. As will be appreciated by persons skilled in the relevant art, CPU 1120 also may be a single processor in a multi-core/multi-processor system, such system operating alone, or in a cluster of computing devices operating in a cluster or server farm. CPU 1120 may be connected to a data communication infrastructure 1110, for example, a bus, message queue, network, or multi-core message-passing scheme.

Device 1100 also may include a main memory 1140, for example, random access memory (RAM), and also may include a secondary memory 1130. Secondary memory 1130, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 1130 may include other similar means for allowing computer programs or other instructions to be loaded into device 1100. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to device 1100.

Device 1100 also may include a communications interface ("COM") 1160. Communications interface 1160 allows software and data to be transferred between device 1100 and external devices. Communications interface 1160 may include a modem, a network interface (such as an Ethernet card), a communications port, a PCMCIA slot and card, or the like. Software and data transferred via communications interface 1160 may be in the form of signals, which may be electronic, electromagnetic, optical, or other signals capable of being received by communications interface 1160. These signals may be provided to communications interface 1160 via a communications path of device 1100, which may be implemented using, for example, wire or cable, fiber optics, a phone line, a cellular phone link, an RF link or other communications channels.

Device 1100 also may include input and output ports 1150 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware.

The tools, modules, and functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples be considered as exemplary only.

What is claimed is:

1. An image processing method, comprising:
    identifying, using a machine learning system, an area of interest of a target image by analyzing microscopic features extracted from multiple image regions in the target image, the machine learning system being generated by processing a plurality of training images each comprising an image of human tissue and a diagnostic label characterizing at least one of a slide morphology, a diagnostic value, a pathologist review outcome, and an analytic difficulty;
    determining, using the machine learning system, a probability of a target feature being present in the area of interest of the target image based on an average probability;
    determining, using the machine learning system, a prioritization value, of a plurality of prioritization values, of the target image based on the probability of the target feature being present in the target image, the prioritization value comprising a first prioritization value determined based on preferences of a first user and a second prioritization value determined based on preferences of a second user; and
    ordering, using the machine learning system, a plurality of digitized pathology images based on the plurality of prioritization values associated with the digitized pathology images, and a placement of the target image based on the prioritization value of the target image based on the target feature.

2. The method of claim 1, wherein the diagnostic label comprises a preparation value corresponding to a likelihood that further preparation is to be performed by preparing a new slide for the target image.

3. The method of claim 2, wherein further preparation is performed by preparing a new slide for the target image based on at least one of a specimen recut, an immunohistochemical stain, additional diagnostic testing, additional consultation, and/or a special stain, being performed prior to a user review.

4. The method of claim 1, further comprising: upon determining that the target feature comprises a feature in the target image indicating that further preparation is to be performed, preparing a new slide for the target image prior to a user review.

5. The method of claim 4, the diagnostic feature comprising at least one of cancer presence, cancer grade, treatment effects, precancerous lesions, biomarkers for treatment selection, and/or presence of infectious organisms.

6. The method of claim 1, wherein the diagnostic label comprises an artifact label corresponding to at least one of scanning lines, missing tissue, and/or blur.

7. An image processing system, comprising:
    a memory storing instructions; and
    a processor configured to execute the instructions to perform operations comprising:
    identifying, using a machine learning system, an area of interest of a target image by analyzing microscopic features extracted from multiple image regions in the target image, the machine learning system being generated by processing a plurality of training images each comprising an image of human tissue and a diagnostic label characterizing at least one of a slide morphology, a diagnostic value, a pathologist review outcome, and an analytic difficulty;
    determining, using the machine learning system, a probability of a target feature being present in the area of interest of the target image based on an average probability;
    determining, using the machine learning system, a prioritization value, of a plurality of prioritization values, of the target image based on the probability of the target feature being present in the target image, the prioritization value comprising a first prioritization value determined based on preferences of a first user and a second prioritization value determined based on preferences of a second user; and
    ordering, using the machine learning system, a plurality of digitized pathology images based on the plurality of prioritization values associated with the digitized pathology images, and a placement of the target image based on the prioritization value of the target image based on the target feature.

8. The system of claim 7, wherein the diagnostic label comprises a preparation value corresponding to a likelihood that further preparation is to be performed by preparing a new slide for the target image.

9. The system of claim 7, wherein further preparation is performed for the target image based on at least one of a specimen recut, an immunohistochemical stain, additional diagnostic testing, additional consultation, and/or a special stain, being performed prior to a user review.

10. The system of claim 7, wherein the diagnostic label comprises a diagnostic feature of the target image.

11. The system of claim 10, the diagnostic feature comprising at least one of cancer presence, cancer grade, treatment effects, precancerous lesions, biomarkers for treatment selection, and presence of infectious organisms.

12. The system of claim 7, wherein the diagnostic label comprises an artifact label corresponding to at least one of scanning lines, missing tissue, and blur.

13. A non-transitory computer-readable medium storing instructions that, when executed by at least one processor, cause the at least one processor to perform an image processing method, the method comprising:
- identifying, using a machine learning system, an area of interest of a target image by analyzing microscopic features extracted from multiple image regions in the target image, the machine learning system being generated by processing a plurality of training images each comprising an image of human tissue and a diagnostic label characterizing at least one of a slide morphology, a diagnostic value, a pathologist review outcome, and an analytic difficulty;
- determining, using the machine learning system, a probability of a target feature being present in the area of interest of the target image based on an average probability;
- determining, using the machine learning system, a prioritization value, of a plurality of prioritization values, of the target image based on the probability of the target feature being present in the target image, the prioritization value comprising a first prioritization value determined based on preferences of a first user and a second prioritization value determined based on preferences of a second user; and
- ordering, using the machine learning system, a plurality of digitized pathology images based on the plurality of prioritization values associated with the digitized pathology images, and a placement of the target image based on the prioritization value of the target image based on the target feature.

14. The non-transitory computer-readable medium of claim 13, wherein the diagnostic label comprises a preparation value corresponding to a likelihood that further preparation is to be performed by preparing a new slide for the target image.

15. The non-transitory computer-readable medium of claim 14, wherein further preparation is performed by preparing a new slide for the target image based on at least one of a specimen recut, an immunohistochemical stain, additional diagnostic testing, additional consultation, and/or a special stain, being performed prior to a user review.

16. The non-transitory computer-readable medium of claim 13, wherein the diagnostic label comprises a diagnostic feature of the target image, the diagnostic feature comprising at least one of cancer presence, cancer grade, treatment effects, precancerous lesions, biomarkers for treatment selection, and/or presence of infectious organisms.

* * * * *